United States Patent [19]
Berliner et al.

[11] Patent Number: 5,965,552
[45] Date of Patent: Oct. 12, 1999

[54] ANDROSTANE STEROIDS AS NEUROCHEMICAL INITATORS OF CHANGE IN HUMAN HYPOTHALAMIC COMPOSITIONS AND METHODS

[75] Inventors: David L. Berliner, Atherton, Calif.; Nathan William Adams; Clive L. Jennings-White, both of Salt Lake City, Utah

[73] Assignee: Pherin Pharmaceuticals, Inc., Menlo Park, Calif.

[21] Appl. No.: 09/212,735

[22] Filed: Dec. 15, 1998

Related U.S. Application Data

[63] Continuation of application No. 08/654,021, May 28, 1996, Pat. No. 5,883,087, which is a continuation of application No. 08/127,908, Sep. 28, 1993, abandoned, which is a continuation-in-part of application No. 07/903,604, Jun. 24, 1992, abandoned, which is a continuation-in-part of application No. 07/708,936, May 31, 1991, abandoned, which is a continuation-in-part of application No. 07/638,185, Jan. 7, 1991, abandoned.

[51] Int. Cl.[6] ............................................. A61K 31/565
[52] U.S. Cl. ............................................................ 514/182
[58] Field of Search ............................................. 514/182

[56] References Cited

U.S. PATENT DOCUMENTS

| | | | |
|---|---|---|---|
| 3,413,321 | 11/1968 | Boswell et al. | 260/397 |
| 3,681,490 | 8/1972 | Melrose et al. . | |
| 3,908,007 | 9/1975 | Itel et al. | 424/242 |
| 3,960,841 | 6/1976 | Engel et al. . | |
| 4,071,624 | 1/1978 | Grunwell et al. . | |
| 4,071,625 | 1/1978 | Grunwell . | |
| 4,075,233 | 2/1978 | Marx et al. . | |
| 4,087,524 | 5/1978 | Grunwell et al. . | |
| 4,133,811 | 1/1979 | Varma . | |
| 4,139,617 | 2/1979 | Grunwell et al. . | |
| 4,210,644 | 7/1980 | Ewing et al. | 424/239 |
| 4,239,681 | 12/1980 | Grunwell et al. . | |
| 4,315,925 | 2/1982 | Hussain et al. | 424/239 |
| 4,330,538 | 5/1982 | Itil et al. | 424/238 |
| 4,349,474 | 9/1982 | Chinn . | |
| 4,425,339 | 1/1984 | Pitchford . | |
| 4,738,957 | 4/1988 | Laurent et al. | 514/182 |
| 4,835,147 | 5/1989 | Roberts . | |
| 4,863,911 | 9/1989 | Anderson et al. . | |
| 5,089,482 | 2/1992 | Hermens et al. | 514/58 |
| 5,108,995 | 4/1992 | Casper | 514/170 |
| 5,155,045 | 10/1992 | Cutler et al. . | |
| 5,272,134 | 12/1993 | Berliner | 512/3 |
| 5,278,141 | 1/1994 | Berliner | 512/3 |
| 5,303,703 | 4/1994 | Monti-Bloch | 128/642 |
| 5,883,087 | 3/1999 | Berliner et al. | 514/182 |

FOREIGN PATENT DOCUMENTS

| | | | |
|---|---|---|---|
| 2295916 | 12/1990 | Japan . | |
| WO 94/28903 | 12/1994 | WIPO | A61K 31/56 |
| WO 94/28904 | 12/1994 | WIPO | A61K 31/56 |

OTHER PUBLICATIONS

"Offaction in Human with special reference to odorous 16–androstenes: their occurance, perception and possible social, psychological and sexual impact", *Chemical Abstracts*, vol. 118, No. 25, 1992, see abstract No. 247775p, J. Endocrin., 137 (2), 167–168.

Garcia–Velasco et al., *Aesth. Plast. Surg.* 19:451–454, 1995.

Axel, *Scientific American*, Oct. 1995 pp. 154–159.

A.A. Hussain et al., "Administering natural Female Sex Hormones", *Pharmaceuticals*, vol. 96, p. 421, No. 96:187314c, (1982).

Agosta, W.C., "Chemical Communication (The Language of Pheromes)", *Scientific American Library*, New York, Chapter 6, pp. 130–140, (1992).

Axel, Richard, "The Molecular Logic of Smell," *Scientific American*, Oct. 1995 pp. 154–159.

Beauchamp, et al., "The pheromone concept in mammalian chemical communications: A Critique," *Mammalian Offaction Reproductive Processes, and Behavior*, Doty, RLL, Ed., Academic Press, New York, pp. 143–160, (1976).

Bird, et al., Estimation of the odorous steroid, 5 alpha–androst–16–en–3–one, in human saliva CA:99(1):64581a, (1983).

Brooksbank, et al., "Fate of Androsta–4, 15–dien–3–one and the origin of 3α–hydroxy–5αansrost–6–ene in man," *J. Endocr.*, (1972) vol. 52, pp. 239–251.

Chakravarti, et al. (1979), CA 91:134649f.

Chakravarti, et al., Relation between plasma hormone profiles, symptoms, and response to estrogen treatment in women approaching the menopause, CA 91–124649f, (1979).

Claus et al., "The boar–pheromone steroid identified in vegetables,", *Experiemtia*, (1979) vol. 25, pp. 1674–1675.

Claus et al., "Occurrence of 5α–androst–16–en–3–one, a boar pheromone, in man and its relationship to testosterone," *J. Endocr.*, (1976)) vol. 68, pp. 483–484.

Foreman, et al., "Preclinical studies on quinelorane, a potent and highly selective Dx–dopamineric agonist" *J. Pharmacology and Experimental Therapeutics*, (1989) vol. 250, No. 1, pp. 227–235.

García–Velasco et al., "Nose Surgery and the Vomeronasal Organ, " *Aesth. Plast. Surg. 19* 51–454, 1995.

(List continued on next page.)

*Primary Examiner*—Jose' G. Dees
*Assistant Examiner*—Barbara Badio
*Attorney, Agent, or Firm*—Heller Ehrman White & McAuliffe

[57] ABSTRACT

The invention relates to a method of altering hypothalamic function in an individual. The method comprises nasally administering a human semiochemical, e.g. an Androstane steroid, or a pharmaceutical composition containing a semiochemical, such that the ligand semiochemical binds to a specific neuroepithelial receptor. The steroid or steroids is/are preferably administered in the form of a pharmaceutical composition containing one or more pharmaceutically acceptable carriers. Other embodiments of the invention include pharmaceutical compositions containing the steroids.

12 Claims, 10 Drawing Sheets

OTHER PUBLICATIONS

García–Velasco et al., "The incidence of the vomeronasal organ in 1000 human subjects and its possible clinical significance," *J. Steroid Biochem. and Molec. Biol.,* (1991), vol. 39, No. 4B, pp. 561–563.

Gower, et al., "The significance of odorous steroids in axillary odour," *Perfumery: the Psychology and Biology of Fragrance,* Van Toller et al., Eds, Chapman and Hall, London, pp. 47–75 (1988).

Hussain, A.A. et al., "Administering Natural Female Sex Hormones," *Pharmaceuticals,* (1982) vol. 96, p. 421, No. 96:187314c.

Johnson, et al., "Clinical and histological evidence for the presence of the vomeronasal (Jacobson's) organ in adult humans," *J. Otolaryngology,* (1985) vol. 14, No. 2, pp. 71–79.

Kirk–Smith et al., "Human social attitudes affected by androstenol," *Research Communications in Psychology, Psychiatry, and Behavior,* (1978) vol. 3, No. 4, pp. 379–384.

Kwan et al., "15–androstenes, putative pheromones in human semen," *Med. Sci Res.,* (1987) vol. 15, pp. 1443–1444.

Lauber et al. (1990) CA 113:165668p.

Li, Ruisheng, et al., "Two polyhydroxylated steroids from the Chinese soft coral *Litophyton arboreum,*" *Steriods,* Aug. 1994, vol. 59, pp. 503–505.

Melrose et al., "Androgen–steroids associated with boar odour as an aid to the detection of oestrus in pig artificial insemination," *Br. Vet. J.,* (1971) vol. 127, pp. 497–502.

The Merck Index, 11th Ed., "Estone," No. 3660, (1989).

The Merck Manual, 14th Ed., (1982) pp. 1633–1635.

Michael, et al., "Pheromones in the Communication of Sexual Status in Primates," May 25, 1968, *Nature,* vol. 218, pp. 746–749.

Monti–Bloch, et al., "Effect of Putative pheromones on the electrical activity of the human vomeronasal organ and olfactory epithelium," *J. Steroid Biochem, and Molec. Biol.* (1991) vol. 39, No. 4B, pp. 573–582.

Moran et al., The vomeronasal (Jacobson's) organ in man: Ultrastructure and frequency of occurrence, *J. Steroid Biochem. and Molec. Biol.,* (1991) vol. 29, 4B, pp. 545–552.

Muller–Schwarze, et al., Eds., *Chemical Signals (Vertebrates and Aquatic Invertebrates*), Plenum Press, New York (1980).

Ohloff, et al., "Structural and configurational dependence of the sensory process in steroids," *Helv Chim. Acta.,* (1983) vol. 66, pp. 192–217.

Parrott, R.F., "Homotypical sexual behavior in gonadectomized female and male rates treated with 5α–19–Hydroxytestosterone: Comparison with related androgens," *Hormones & Behavior,* (1976) vol. 7, pp. 207–215.

Perry, et al. "Pig courtship behavior: pheromonal property of androstene steroids in male submaxillary se retion," (1980), CA 94:45007q.

Pheonix, C.H., "Sexual behavior of castrated male rhesus monkeys treated with 19–Hydroxytestosterone," *Physiology & Behavior,* (1976) vol. 15, pp. 305–310.

Phoenix, C.H. "Induction of sexual behavior in ovariectomized rhesus females with 19–Hydroxytestosterone," *Hormones & Behavior,* (1977) vol. 8, pp. 356–362.

Physicians Desk Reference, 31st Ed., pp. 598–599, *Premarin,* (1977).

Reed, et al., "Androgen steroids as an aid to the detection of oestrus in pig artifical insemination," *Br. Vet. J.,* (1974) vol. 130, pp. 61–65.

Stensaas, et al., "Ultrastructure of the human vomeronasal organ," *J. Steroid Biochem. and Molec. Biol.,* (1991) vol. 39, No. 4B, pp. 553–560.

Terasawa, T., et al., "Convenient Preparative Routes to 19–Hydroxy, 19–0X0–, 19–OIC, and 19–Nor–Deoxycorticosterone," *Tetrahedron,* 1986, vol. 42, No. 2, pp. 537 to 545.

Thompson et al. (1980) CA 94:77415n.

Chemical Abstract, Registry No. 100–30–51–6, vol. 60, No. 3, Feb. 3, 1964.

Hsia et al., "Inhibition of Glucuronosyl Transferase by Steroid Hormones", *Archives of Biochemistry and Biophysics,* 103:181–185 (1963).

ANDROSTANE STEROIDS AS NEUROCHEMICAL INITATORS OF CHANGE IN HUMAN HYPOTHALAMIC COMPOSITIONS AND METHODS

CROSS-REFERENCE TO RELATED APPLICATIONS

This application is a continuation of U.S. application Ser. No. 08/654,021, filed May 28, 1996, now U.S. Pat No. 5,883,087 which is a continuation of Ser. No. 08/127,908, filed Sep. 28, 1993, now abandoned which is a continuation-in-part of U.S. application Ser. No. 07/903,604, filed Jun. 24, 1992, which in turn is a continuation-in-part of U.S. application Ser. No. 07/708,936, filed May 31, 1991, which in turn is a continuation-in-part of U.S. application Ser. No. 07/638,185, filed Jan. 7, 1991, now abandoned.

BACKGROUND

The application also relates to another continuation-in-part of U.S. patent application Ser. No. 07/903,604, U.S. patent application Ser. No. 08/077,359, filed Jun. 15, 1993, and to commonly assigned, co-pending U.S. patent application Ser. No. 07/903,525, filed Jun. 24, 1992 (a continuation-in-part of U.S. application Ser. No. 07/707,862, filed May 31, 1991, which in turn is a continuation-in-part of U.S. Application Serial No. 07/638,743, filed Jan. 7, 1991, now abandoned) entitled "Estrene Steroids as Neurochemical Initiators of Change in Human Hypothalamic Function and Related Pharmaceutical Compositions and Methods"; and to the commonly assigned, continuation-in-part of 07/903,525, U.S. patent application Ser. No. 08/077,140. The aforementioned U.S. patent applications are each incorporated herein by reference.

Finally, this application may relate to a co-pending U.S. patent application entitled "Fragrance Compositions Containing Human Pheromones", filed Mar. 24, 1992, U.S. Ser. No. 07/856,435.

1. Technical Field

This invention relates generally to pharmaceutical compositions and methods for effectuating change in human hypothalamic function, thereby altering certain behavior and physiology mediated by the hypothalamus of individuals. More particularly, the invention relates to the use of certain Androstene steroids as neurochemical effectuators of physiology and behavior.

2. Description of the Related Art

The present invention relates to certain compounds, namely Androstane steroids, particularly Androstene steroids and related compounds as will be described herein, and methods of using these compounds as human semiochemicals in order to alter hypothalamic function, thereby affecting certain consequent behavior and physiology, e.g., the reduction of anxiety. Androstane steroids are typified by testosterone and they are characterized by a four ring steroidal structure, a methylation at the 13-position and at the 10-position. Androstenes are a subset of Androstanes and have at least one double bond. Ohloff, G. et al. (*Helv. Chim. Acta* (1983) 66:192–217), which is incorporated herein by reference, have shown that several members of this group of steroids have an odor which varies with different isomeric, diastereomeric, and enantiomeric forms. Some members of this group have been reported to act as a pheromone in some mammalian species—for instance, $5\alpha$-androst-16-en-3-one and $5\alpha$-androst-16-en-3$\alpha$-ol in pigs (Melrose, D. R., et al., *Br. vet. J.* (1971) 127:497–502). These 16-Androstenes produced by the boar induce mating behavior in estrus sows (Claus, et al., *Experimentia* (1979) 3:1674–1675).

Some studies have noted that, in some species, various characteristics of certain 16-Androstenes (including $5\alpha$-Androst-16-en-3$\alpha$2-ol and $5\alpha$-Androst-16-en-3-one), such as concentration, metabolism, and localization, are sexually dimorphic (Brooksbank et al., *J. Endocr.* (1972) 52:239–251; Claus, et al., *J. Endocr.* (1976) 68:483–484; Kwan, et al, *Med. Sci. Res.* (1987) 15:1443–1444). For instance, $5\alpha$-Androst-16-en-3$\alpha$-ol and $5\alpha$-Androst-16-en-3-one, as well as Androsta-4,16-dien-3-one, have been found at different concentrations in the peripheral blood, saliva and axillary secretions of men and of women (Kwan, T. K., et al., *Med. Sci. Res.* (1987) 15:1443–1444), and their function as a human pheromone, to the extent of affecting choice and judgement, has been suggested (Id; see also Gower, et al., "The Significance of Odorous Steroids in Axillary Odour", In, *Perfumery,* pp. 68–72, Van Toller and Dodd, Eds., Chapman and Hall, 1988); Kirk-Smith, D. A., et al., *Res. Comm. Psychol. Psychiat. Behav.* (1978) .3:379). Androstenol ($5\alpha$-androst-16-en-3$\alpha$-ol) has been claimed to exhibit a pheromone-like activity in a commercial men's cologne and women's perfume (Andron "for men and Andron" for women by Jōvan). Japanese Kokai No. 2295916, refers to perfume compositions containing androstenol and/or its analogues. $5\alpha$-Androstadien-3$\beta$-ol (and perhaps the 3$\alpha$-ol) has also been identified in human axillary secretion (Gower, et al., Supra at 57–60. On the other hand, there is little agreement in the literature as to whether or not any putative pheromone actually plays any role in the sexual or reproductive behavior of mammals, particularly of humans. See:Beauchamp, G. K., et al., "The Pheromone Concept in Mammalian Chemical Communication:A Critique", In:*Mammalian Olfaction, Reproductive Processes and Behavior,* Doty, R. L., Ed., Academic Press, 1976). See, also:Gower, et al., supra at 68–73.

An embodiment of the subject invention concerns the non-systemic, nasal administration of certain Androstane and Androstene steroids to affect a specific behavioral or physiological response in human subjects, e.g., a reduction of negative affect, mood, and character traits. In particular, nasal administration provides for contacting neurochemical receptors of a heretofore poorly understood neuroendocrine structure, commonly known as the vomeronasal organ ("VNO"; also known as "Jacobson's organ"), with one or more steroid(s) or with compositions containing the steroid (s). This organ is accessed through the nostrils of most higher animals—from snakes to humans, and has been associated, inter alia, with pheromone reception in certain species (see generally Muller-Schwarze & Silverstein, *Chemical Signals,* Plenum Press, New York (1980)). The axons of the neuroepithelia of the vomeronasal organ, located supra palatinal, form the vomeronasal nerve and have direct synaptic connection to the accessory olfactory bulb and indirect input from there to the cortico-medial amygdaloid basal forebrain and hypothalamic nuclei of the brain. The distal axons of terminalis nerve neurons may also serve as neurochemical receptors in the VNO. Stensaas, L. J., et al.,*J. Steroid Biochem. and Molec. Biol.* (1991) 39:553. This nerve has direct synaptic connection with the hypothalamus.

Johnson, A. et al. (*J. Otolaryngology* (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., supra; and by Moran, D. T., e al., Garcia-Velasco, J. and M. Mondragon; Monti-Bloch, L. and B. Grosser all in *J. Steroid Biochem. and Molec, Biol.* (1991) 39.

It is apparent that it would be desirable to identify and synthesize human semiochemicals and pheromones and to develop pharmaceutical compositions and methods of use to influence hypothalamic function. This invention relates to the unexpected discovery that, when nasally administered to human subjects, certain neurochemical ligands, particularly Androstane steroids, more particularly Androstene steroids and related compounds, or pharmaceutical compositions containing Androstanes, Androstenes or related compounds, specifically bind to chemoreceptors of certain nasal neuroepithelial cells and this binding generates a series of neurophysiological responses resulting in an alteration of hypothalamic function of an individual. When properly administered, the effect of certain of these compounds on the hypothalamus affects the function of the autonomic nervous system and a variety of behavioral-or physiological phenomena which include, but are not limited to the following: anxiety, premenstrual stress, fear, aggression, hunger, blood pressure, and other behavioral and physiological functions normally regulated by the hypothalamus. Otto Appenzeller. The Autonomic Nervous System. An introduction of basic and clinical concepts (1990); Korner, P. I. Central nervous control of autonomic cardiovascular function, and Levy, N. M. and Martin, P. J. Neural control of the heart, both in Handbook of Physiology; Section 2: Cardiovascular System—the heart, Vol I, Washington DC, 1979, American Physiological Society; Fishman, A.P., et al. editors, Handbook of Physiology. Section 3:Respiratory System. Vol. II. Control of breathing. Bethesda Md. 1986. American Physiological Society.

In some instances a single Androstane steroid, or related compound, is administered, in some instances combinations of Androstane steroids and/or related compounds are administered and in some instances one or more Androstane steroids are co-administered along with one or more Estrane or Estrene steroids or a related compound.

SUMMARY OF THE INVENTION

Accordingly, it is an object of this invention to provide pharmaceutical compositions which contain human semiochemicals or pheromones and are suitable for nasal administration in an. individual.

It is also an object of this invention to provide methods of using these compositions to alter hypothalamic function of an individual.

It is a further object of this invention to provide methods of using these compositions to affect physiological and behavioral functions of individuals which are normally regulated by the hypothalamus.

Finally, it is an object of this invention to provide methods of altering hypothalamic function which have the following advantages:1) administration directly to the chemoreceptors in the nasal passage and the vomeronasal organ, without pills or needles—i.e., non-invasively; 2) a mode of drug action through the nervous system and not through the circulatory system—thus brain function can be affected without consideration of the blood-brain barrier; 3) a direct means of affecting the hypothalamus—there is only one synaptic junction between pheromone receptors and the hypothalamus; and, 4) providing a highly specific drug effect, thereby greatly reducing the potential for undesirable side-effects—this because sensory nerves are addressed to a specific location in the brain.

Additional objects, advantages and novel features of the invention will be set forth in part in the description which follows, and in part will become apparent to those skilled in the art upon examination of the following, or may be learned by practice of the invention.

Objects of this invention are achieved by providing a pharmaceutical composition suitable for nasal administration in an individual. The composition contains a pharmaceutically acceptable carrier and an Androstane steroid with the formula:

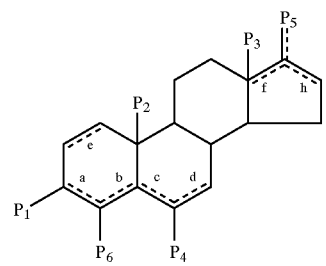

wherein $P_1$ is selected from the group consisting of OXO, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is absent or is selected from the group consisting of methyl, hydroxymethyl, acyloxymethyl, alkoxymethyl, lower alkyl, hydroxyalkyl, acyloxyalkyl, and alkoxylalkyl; $P_4$ is selected from the group consisting of hydrogen, oxo, halo, hydroxy, alkoxy, and acyloxy; $P_5$ represents one or 2 substituents, wherein $P_5$ comprises one or two hydrogen atoms, methyl, methylene, or one or two halo atoms; $P_6$ is hydrogen or halo; and "a", "b", "c", "d", "e", "f", and "h" are alternative sites for optional double bonds.

One class of preferred steroids has "b" as a double bond, particularly wherein "c" or "d" is also a double bond. Another preferred class has "a" and "c" as double bonds. Yet another preferred class contains $P_3$ as a methyl group, "h" as an optional double bond, and $P_5$ as methylene or one or two hydrogen atoms. A class of steroids wherein "a" or "b" is a double bond is also preferred.

By halo, it is meant, F, Cl, Br, or I. The term lower alkyl, lower alkoxy, etc., is meant to encompass carbon chains of 1 to 6 carbon atoms, preferably 1 to 4 carbon atoms.

Other objects of this invention are achieved by providing a method of altering hypothalamic function and/or autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence, whether or not the modified steroids are explicitly disclosed.

BRIEF DESCRIPTION OF THE DRAWINGS

The Compounds in the graphs are:
A=1, 3, 5(10),16-Estratetraen-3-yl acetate
B=Androsta-4,16-dien-3-one
C=1,3,5(10),16-Estratetraen-3-ol
D=3-Methoxy-Estra-1,3,5(10),16-tetraene
E=Androsta-4,16-dien-32-ol
F=Androsta-4,16-dien-3β-ol

G=Androst-4-en-3-one
H=Androsta-4,16-diene-3,6-dione
J=10,17-Dimethylgona-4,13(17)-dien-3-one
K=1,3,5(10),16-Estratetraen-3-ol-methyl ether
L=1,3,5(10),16-Estratetraen-3-yl-propionate
EVG=Electro-vomeronasogram
GSR=Galvanic Skin Response =Electrodermal Activity, EDA
ST=Skin Temperature

M=1,3,5(10)-Estratrien-3-ol

DETAILED DESCRIPTION OF THE INVENTION

I. Definitions

Figure 1:
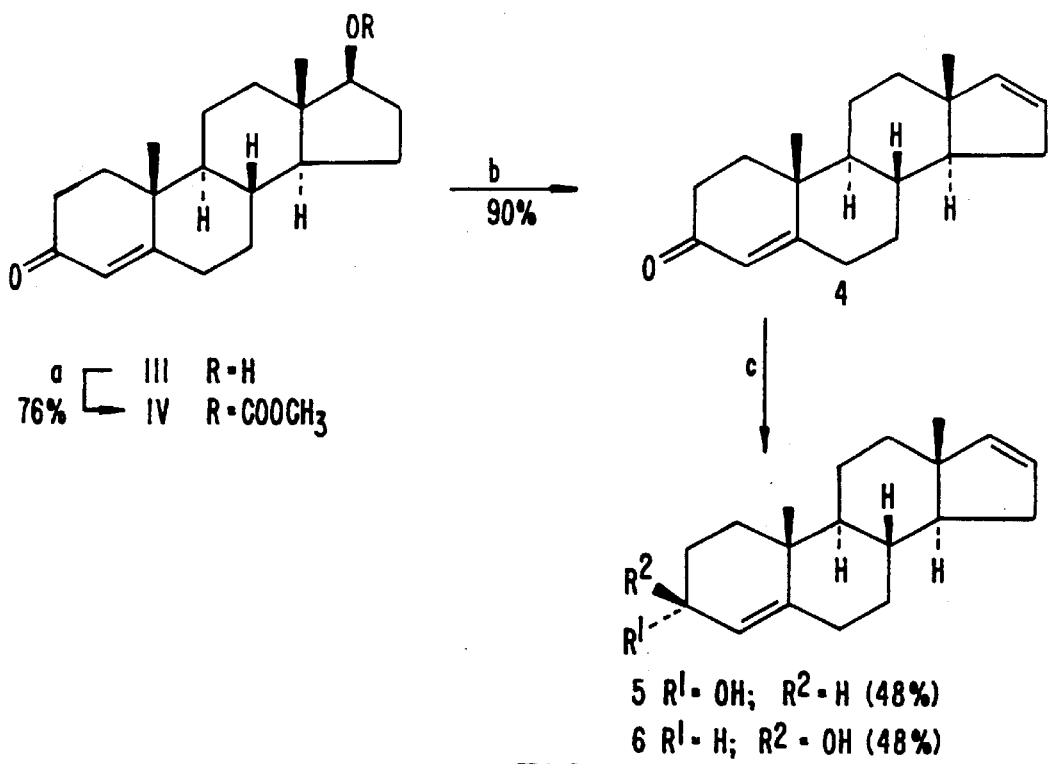
FIG. 1 illustrates the synthesis of Androsta-4,16-dien-3-one, Androsta-4,16-dien-3α-ol, and Androsta-4,16-dien-3β-ol.

An "affect" is a transient feeling state. Typical negative affects are feelings of nervousness, tenseness, shame, anxiousness, irritability, anger, rage, and the like. "Moods" are longer lasting feeling states such as guilt, sadness, hopelessness, worthlessness, remorsefulness, misery, unhappiness and the like. "Character traits" are more permanent aspects of an individual's personality. Typical negative character traits are sensitivity, regretfulness, blameworthiness, stubbornness, resentfulness, bitterness, timidness, laziness and the like.

"Androstane steroids" are aliphatic polycyclic hydrocarbons characterized by a four-ring steroidal structure with a methylation at the 10- and 13-positions. An Androstene is a subset of Androstanes commonly understood to mean that the compound has at least one double bond. Commonly, unless a compound is described as a gonane, it is understood that the compound has an 18-carbon group. However, it is intended herein that 18-Nor-Androstanes are herein regarded as 16-Androstane steroids. Furthermore, all derivatives which have the structural characteristics described above are also referred to generically as Androstane steroids.

A "chemoreceptor" is a receptor molecule displayed on the surface of a "chemosensory" neuroepithelial cell which binds in a stereospecific fashion to a particular ligand or ligands. This specific binding initiates a signal transduction which initiates an afferent nerve impulse. Chemoreceptors are found, inter alia, in taste buds, olfactory epithelium and vomeronasal tissue. "Estrene steroids", as the term is used herein, are aliphatic polycyclic hydrocarbons with a four-ring steroidal structure, at least one double bond in the A-ring, no methylation at the 10-position and an oxo, hydroxyl or hydroxyl derivative such as an alkoxy, ester, benzoate, cypionate, sulfate or glucuronide, at the 3-position. Derivatives which contain these structural characteristics are also referred to generically as Estrene steroids.

The following structure shows the four-ring steroidal structure common to Androstane and Estrene steroids. In describing the location of groups and substituents, the following numbering system will be employed:

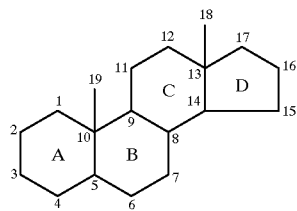

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to an individual in need of the drug. In the present case, a needy individual is one with a physiological or behavioral trait which is normally regulated by the hypothalamus and wherein it is desirable to affect the function of the hypothalamus or the trait. The effective amount of a given drug may vary depending upon the function to be affected, the desired effect, route of administration, and the like. For example, when the steroid is administered as a solution applied to the facial skin of a subject an effective concentration is from 1 microgram/ml to 100 μg/ml, preferably 10 to 50 μg/ml and most preferably 20 to 30 μg/ml. When the steroid is introduced directly into the VNO an effective amount is about 1 picogram to about 1 nanogram, more preferably about 10 picograms to about 50 picograms. When the steroid is administered to the nasal passage, by ointment, cream or aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammillary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the semiochemical therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a semiochemical) a summated change in cell surface receptor potential can be measured.

As used herein, "lower alkyl" means a branched or unbranched saturated hydrocarbon chain of 1 to 4 carbons, such as, for example, methyl, ethyl, n-propyl, i-butyl and the like. "Alkoxy" as used herein is used in its conventional sense to mean the group —OR wherein R is alkyl as herein defined.

A "pheromone" is a substance that provides chemical means of communication between members of the same species through secretion and nasus reception. In mammals pheromones are usually detected by receptors in the vomeronasal organ of the nose. Commonly, pheromones effect development, reproduction and related behaviors. A "semiochemical" is a more general term which includes pheromones and describes a substance from any source which functions as a chemosensory messenger, binds to a specific neuroepithelial receptor, and induces a physiological or behavioral effect. A "vomeropherin" is a semiochemical whose physiologic effect is mediated through the vameronasal organ.

A picogram (pg) is equal to 0.001 nanograms (ng). A ng is equal to 0.001 micrograms (μg). A μg is equal to 0.001 mg.

II. Modes for Carrying Out the Invention

A. Androstanes Useful in the Invention

The invention is directed to a group of certain Androstane steroids. Testosterone (17-hydroxy-Androsta-4-en-3-one) is a typical Androstane.

Androstanes especially suitable for use in the present invention include those where, independently, $p_1$=oxo, α-hydroxy, β-hydroxy; $P_2$=methyl, lower alkyl, hydroxymethyl, hydroxyalkyl; $P_3$=hydrogen or methyl; $P_4$=hydrogen, hydroxy, or oxo; $P_5$=hydrogen or methyl; and there is at least one double bond, asually at the 4- or 16-position.

Preferred Androstanes include Androsta-4,16-dien-3-one ($P_1$=oxo, a=double bond, $P_2$=methyl, $P_3$, $P_4$, $P_5$=hydrogen, commercially available from Steraloids, Inc.), Androsta-4,16-dien-3β-ol ($P_1$=β-OH, a=double bond, $P_2$=methyl, $P_3$, $P_4$, $P_5$=hydrogen), and 6-keto-Androsta-4,16-diene-3-one ($P_1$=oxo, a=double bond, $P_2$=methyl, $P_3$, $P_5$=hydrogen, $P_4$=oxo), synthesis of which are described herein.

A subset of Androstanes within the group are believed to be novel. Syntheses are described herein for the following compounds as designated on the chart:17-methylene-Androst-4-en-3β-ol (A3/N3), 17-methylene-Androst-4-en-3α-ol (A4/N3), 17-methylene-6-oxo-Androst-4-en-3-one (A6/N3), and 6β-OH-Androsta-4,16-dien-3-one (All/N1).

Chart 1 includes androstanes to which the invention is directed, but do not limit its scope. The synthesis diagrams that follow depict intermediate and substructure syntheses for the preparation of these androstanes:

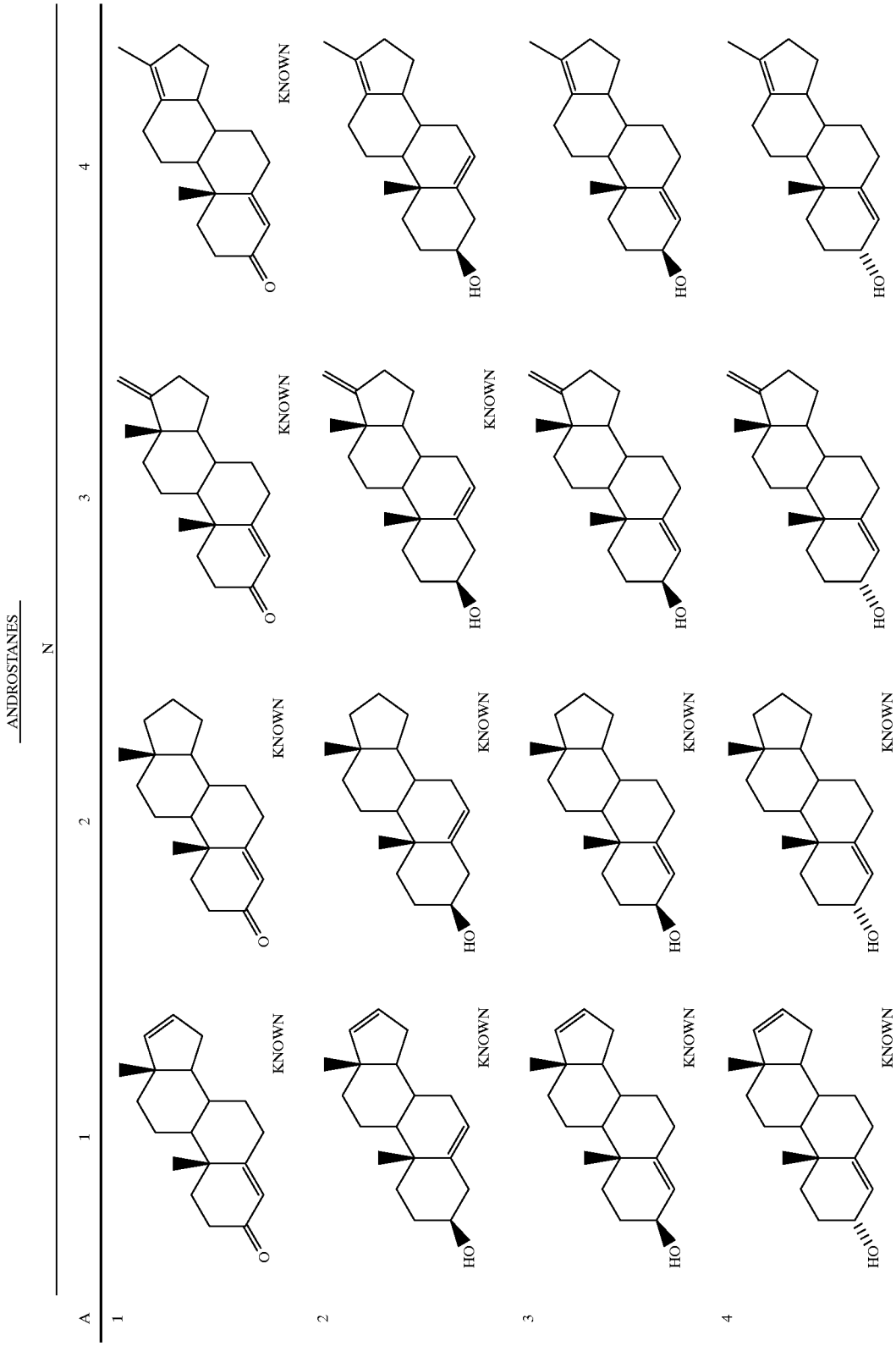

CHART 1-continued
ANDROSTANES
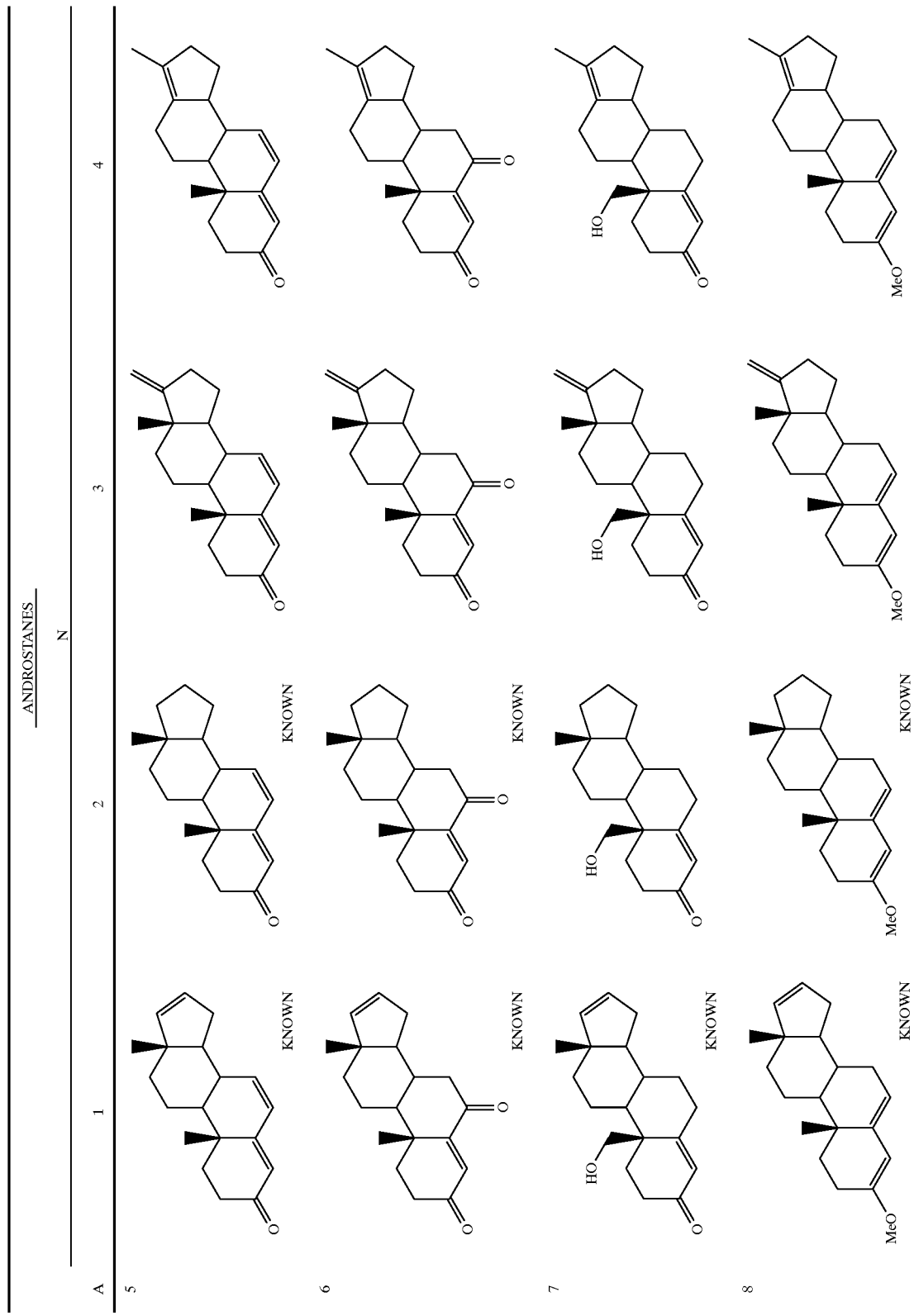

CHART 1-continued
ANDROSTANES
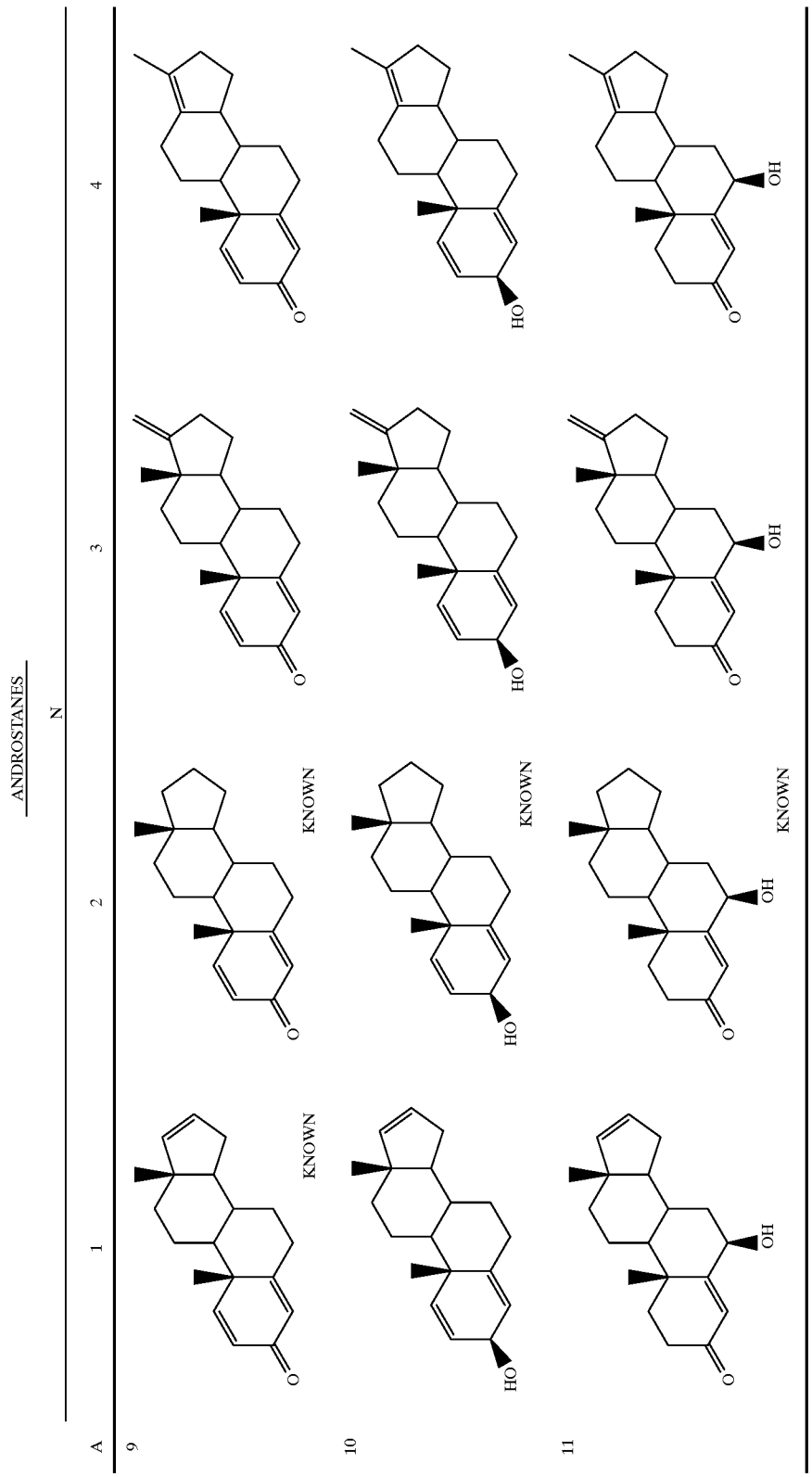

Substructure Syntheses
Referring to the preceding table, the following are exemplary syntheses for intermediates in a given row (A1 through A11) or column (N1 through N4).
A1:
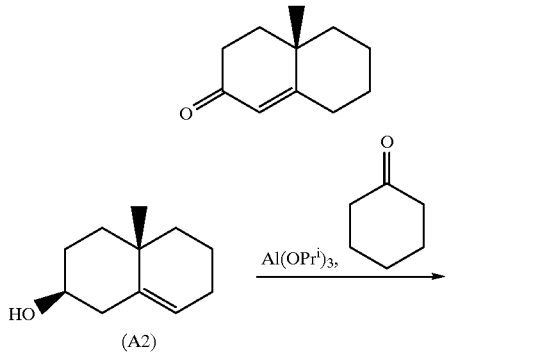
A2:
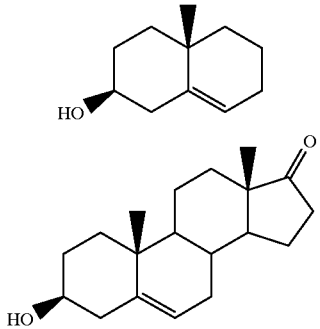
This is a commercially available substructure, for example, DEHYDRO EPI ANDROSTERONE.
A3:
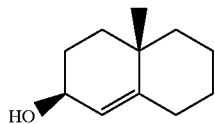
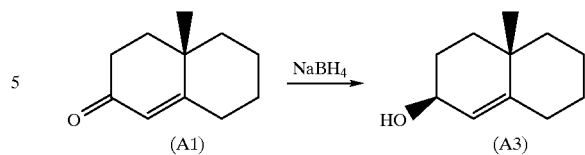
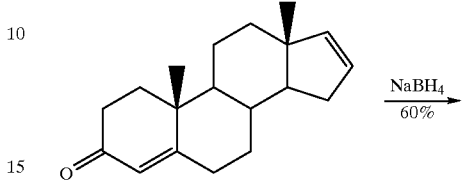
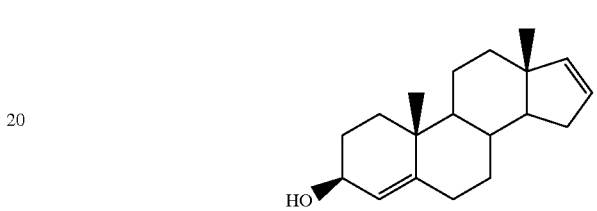
(Michio Matsui and David K. Fukushima, *J.. Org. Chem.*, 1970, Vol. 35, No. 3, p. 561–564).
A4:
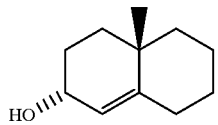
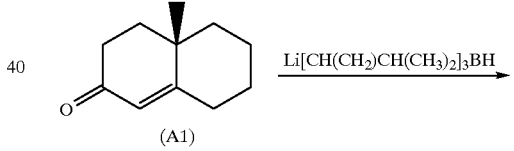
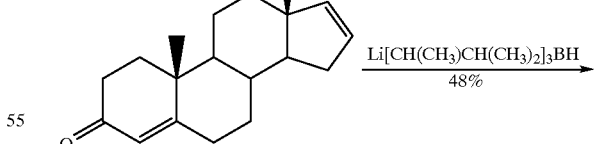
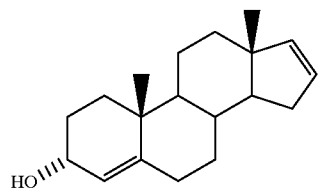

Ohloff, G. et al. (*Helv. Chim. Acta* (1983) 66:192–217).
A5:
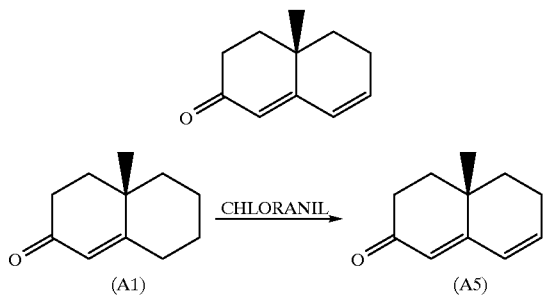
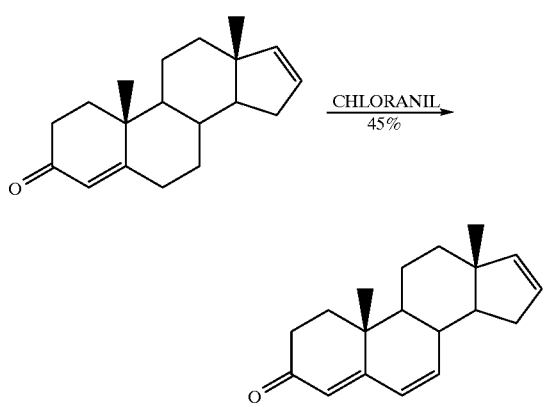
German Off. 2,631,915.
A6:
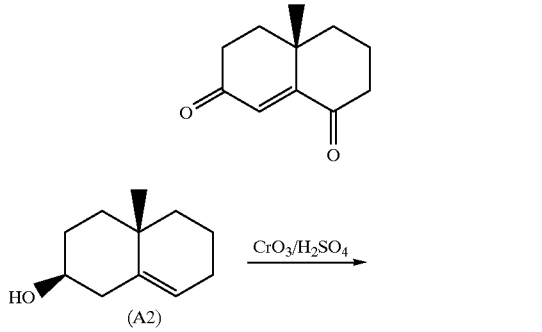
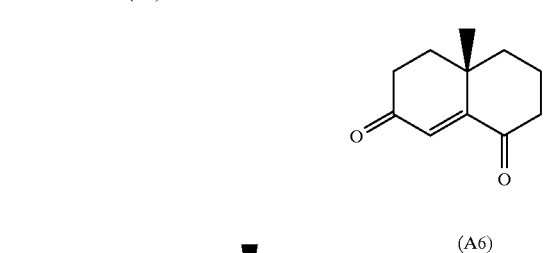
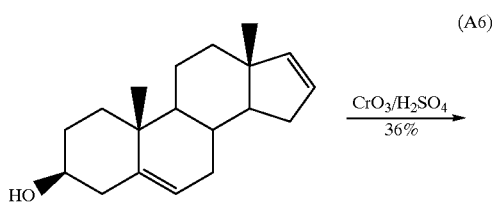
-continued
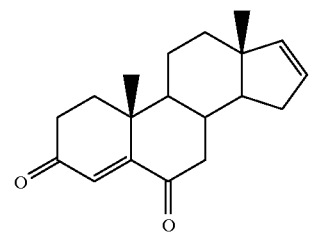
J. Römer, H. Wagner, and W. Sihade, Steroids, 1988, 51/5–6, p. 577–581).
A7:
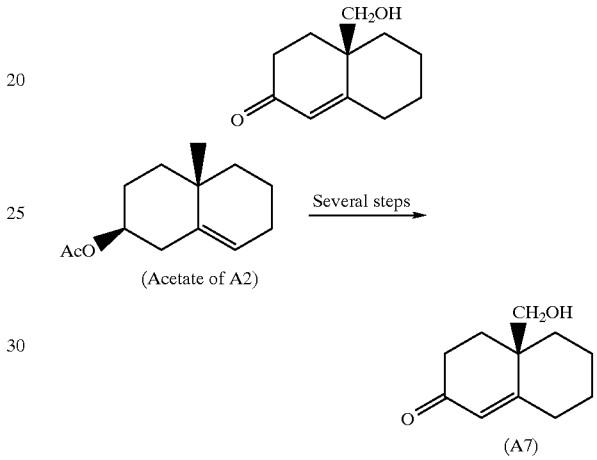
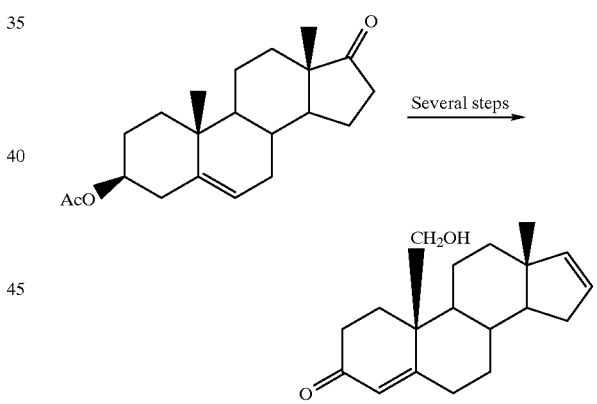
(Habermehl, et al., *Z. Naturforsch.* (1980) 256:191–195).
A8:
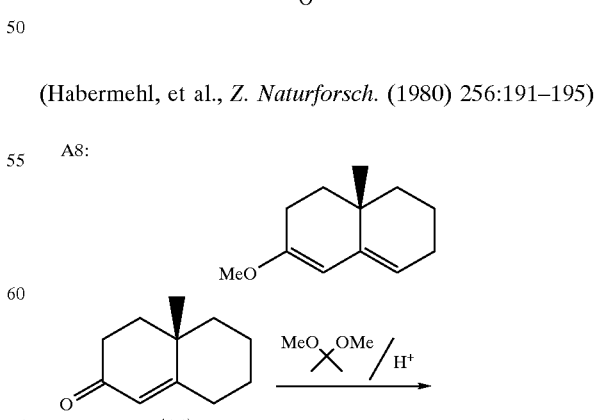

-continued
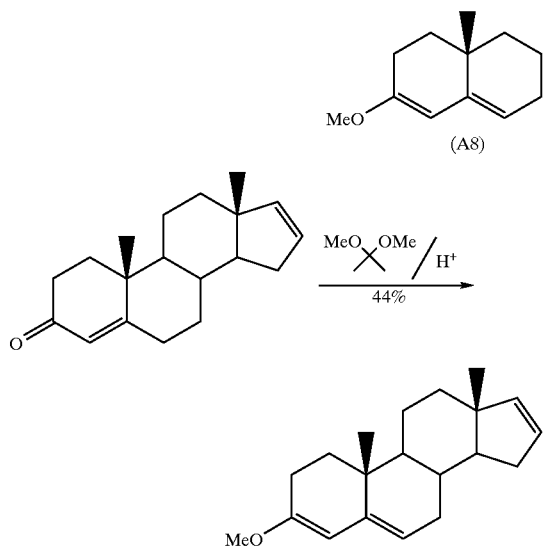
SEE Example 15
A9:
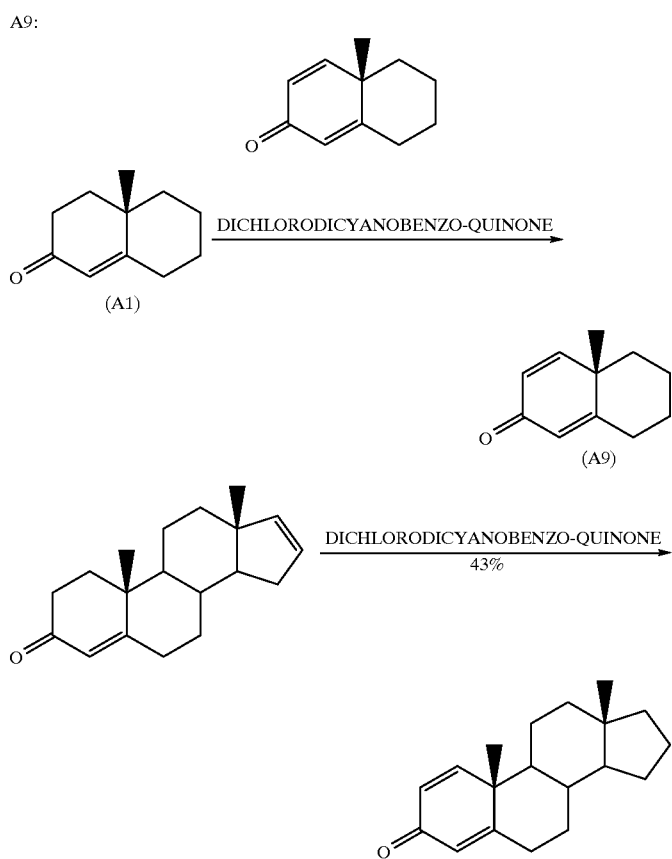
Ohloff, G. et al. (*Helv. Chim. Acta* (1983) 66:192–217).
A10:
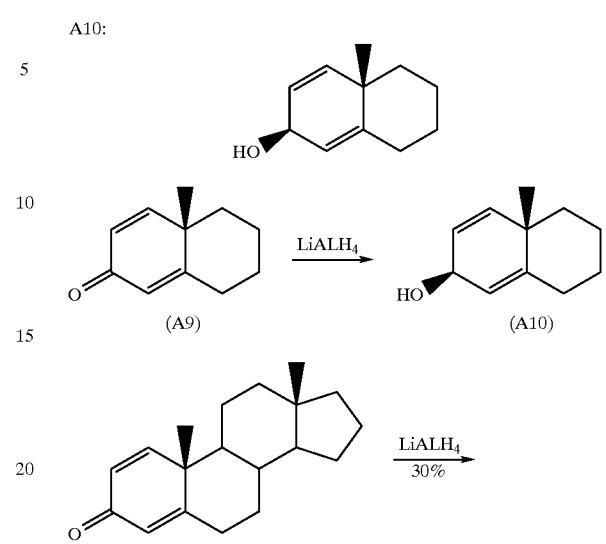

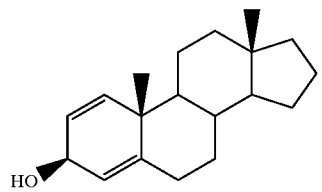
V. I. Mel'nikova and K. K. Pivnitskii, Zhurnal Organickeskoi Khisnii, 1972, Vol. 8, No. 1, pp. 68–74).
A11:
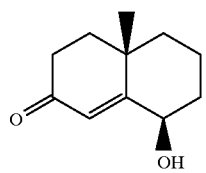
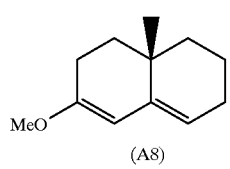
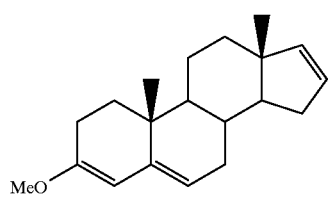
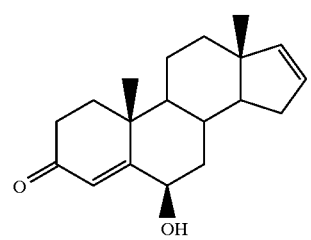
See Example 19
Type N
N1:
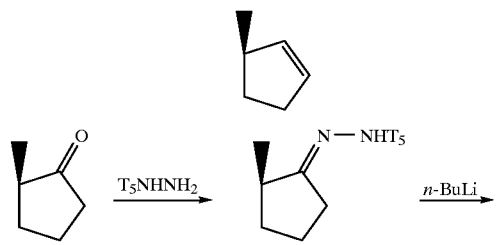
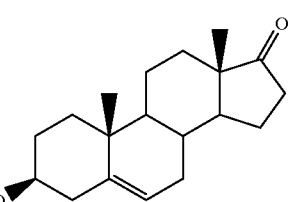
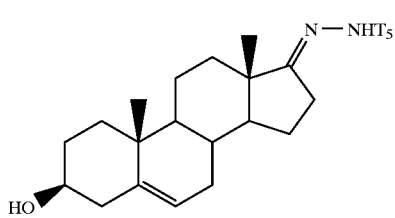
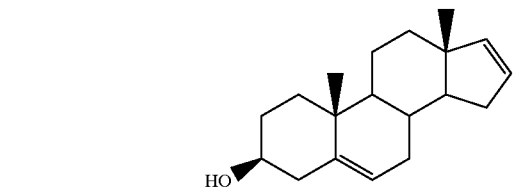
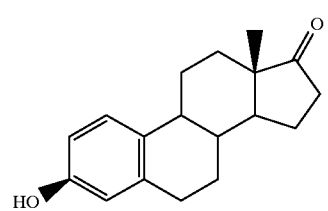
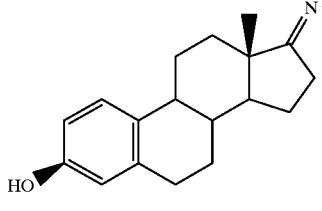
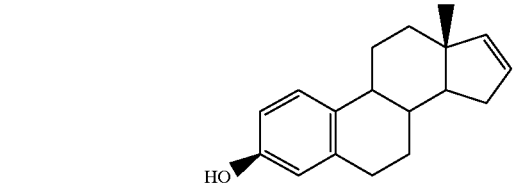
N2:
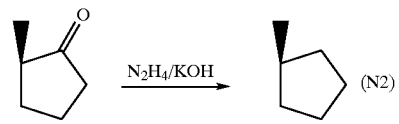
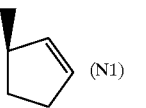

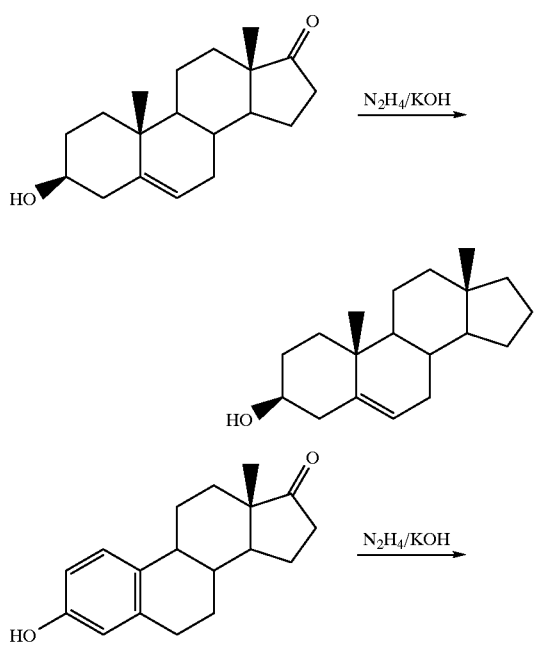
1. Robert H. Shapiro and Carl Djerassi, J. Am. Chem. Soc., 1964, 86, 2825.
2. Pilar Lupon, Frances C. Canals, Arsenio Iglesias, Joan C. Ferrer, Albert Palomar, and Juan-Julio Bonet, J. Org. Chem. 1988, 53, 2193-2198.
N3:
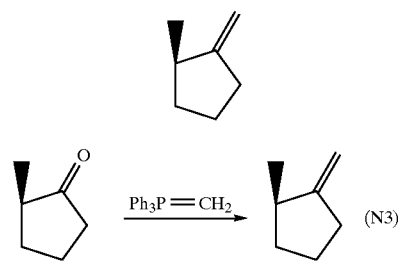
as in
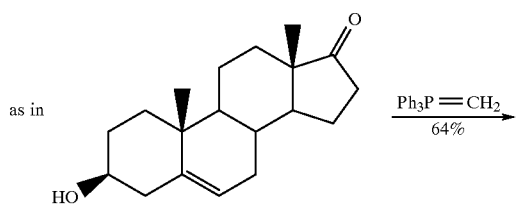
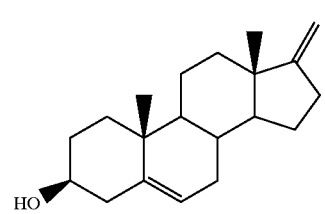
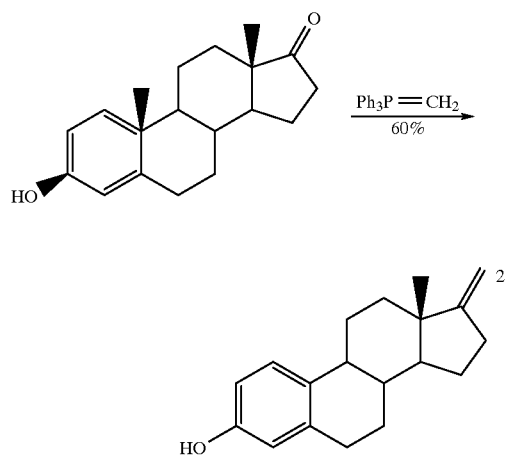
1. Gunther Drefahl, Kurt Ponold and Hans Schick, Berichete, 1965, 98, 604.
2. Richard H. Peters, David F. Crows, Mitchell A. Avery, Wesley K. M. Chong, and Masako Tanabe, J. Med. Chem., 1989, 32, 1642.
N4:
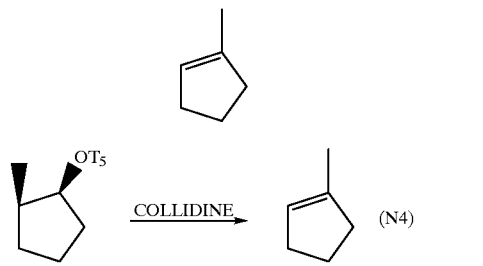
as in
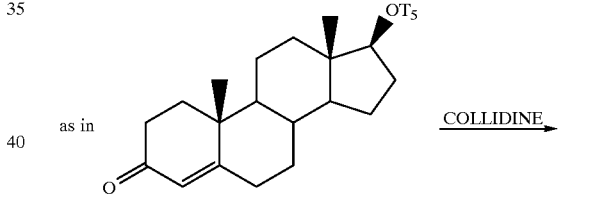
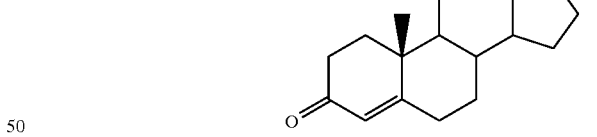
and
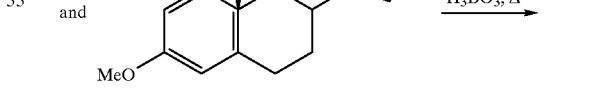

-continued

1. Franz Sondheimer, O. Mancera, M. Urquiza & G. Rosenkranz, J. Am. Chem Soc., 1955, 77, 4145.
2. Williams F. Johns, J. Org. Chem., 1961, 26, 4583.

Methylandrostenes

German Off. 2,631,915 teaches preparation of

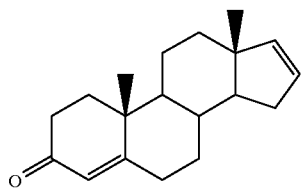

with a methyl group at any one of the following positions: 1α, 2α, 4, 6α, 6β, 7α, and 16.

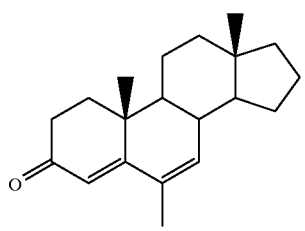

6-METHYLANDROSTA-4,6-DIEN-3-ONE

German Off. 2,428,679.

Syntheses of the 17-METHYLANDROSTENES

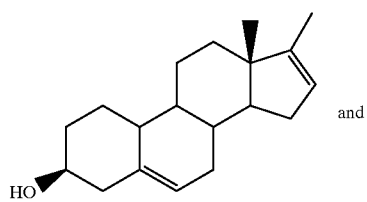

and

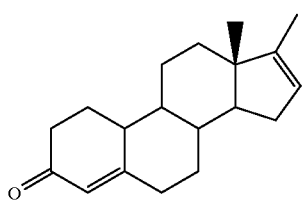

Daniel Bertin and Lucien Nedelac, Mémoires Présentes a la Société Chimique, 1964, No. 345, p. 2140.

Synthesizable compounds therefore include these, together with those derived from them; i.e., N1 with methyl at 1α, 2α, 4, 6α, 66, 7α, 16 or 17 combined with A1, A3, A4, A5, A8, A9, A10 or A11, as well as A2 or A6 with a 17-methyl.

Haloandrostenes

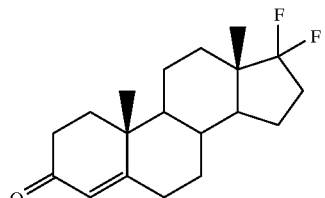

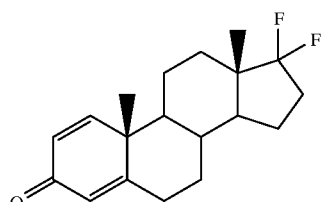

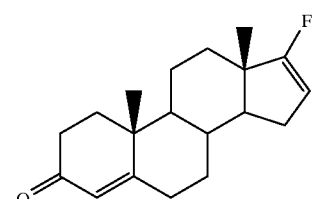

U.S. Pat. No. 3,413,321.

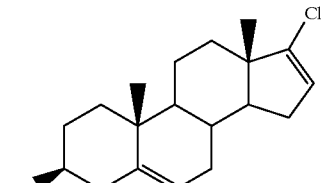

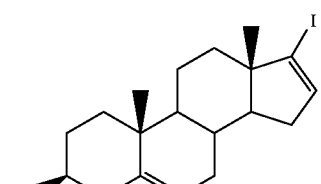

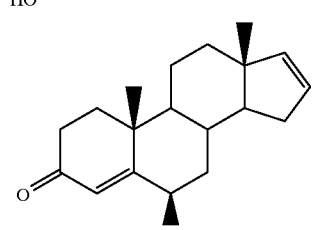

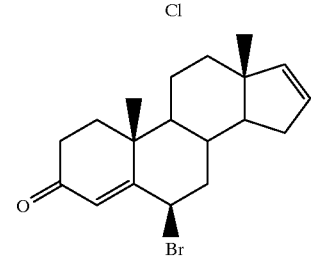

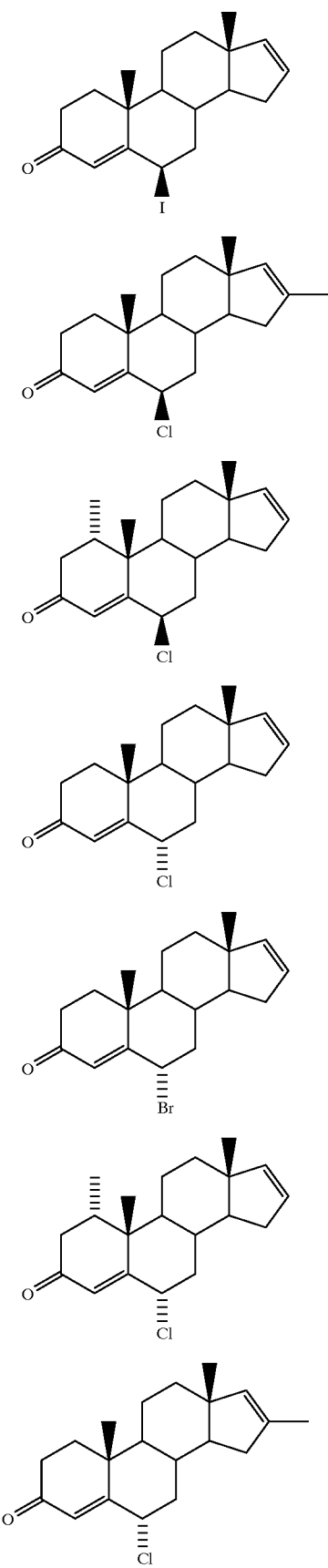

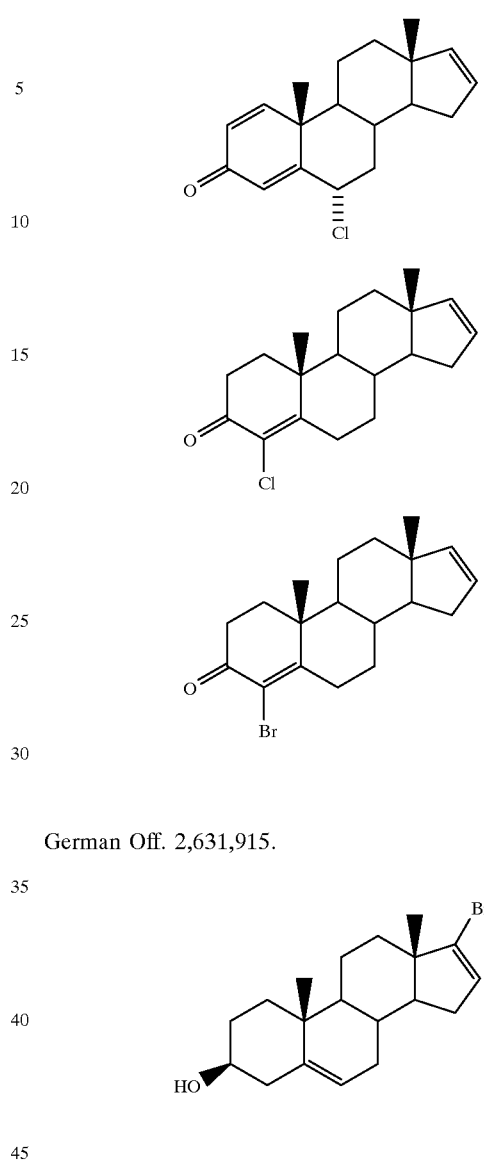

German Off. 2,631,915.

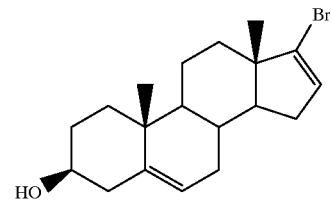

European Patent Application EP 208,497.

Synthesizable compounds therefore include these, together with those derived from them; i.e., (4-Chloro, 4-Bromo, 6α-Chloro, 6α-Bromo, 6β-Chloro, 6β-Bromo, or 6β-Iodo)-A1 in combination with N1, N2, N3, or N4. In addition, (17-Fluoro, 17-Chloro, 17-Bromo, or 17-Iodo)-N1 in combination with A1, A2, A3, A4, A5, A6, A8, A9, A10 or A11.

B. Estrenes Useful in the Invention

The invention is additionally directed to compositions and methods involving the combination of the aforementioned Androstane steroids with certain Estrene steroids which are structurally related to Estradiol (also referred to as 1,3,5 (10)-Estratriene-3,17β-diol). Estrene steroids useful in this invention have the formula:

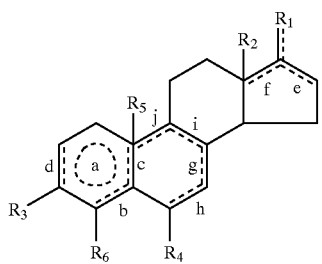

wherein $R_1$ is selected from the group consisting essentially of one or two hydrogen atoms, methyl, methylene, and one or two halo atoms; $R_2$ is absent or is selected from the group consisting essentially of hydrogen and methyl; $R_3$ is selected from the group consisting essentially of oxo, hydroxy, lower alkoxy, lower acyloxy, benzoyl, cypionyl, glucuronide and sulfonyl; $R_4$ is selected from the group consisting essentially of hydrogen, hydroxy, lower alkoxy, lower acyloxy and halo; $R_5$ is absent or is selected from the group consisting essentially of hydrogen, hydroxy, lower alkoxy and lower acyloxy; $R_6$ is a hydrogen or a halo; and "a" represents optional aromatic unsaturation of ring A of said steroid, or "b", "c", and "d" are each optional double bonds; and "e", "f", "g", "h", "i" and "j" are each optional double bonds. In this embodiment, the steroid is preferably administered in the form of a pharmaceutical composition containing one or more pharmaceutically acceptable carriers.

A preferred class of compounds are those in which "a" is present and "g", "h"or "i" are optional double bonds. The class wherein "h" and "i" are both double bonds is also preferred. Another preferred class contains "b", "c"or "j" as a double bond. Yet another class contains "c" and "d" as double bonds. Still another class contains $R_2$ as methyl and (1) "e" as a double bond, (2) $R_1$ is methylene or a single hydrogen, or (3) "f" is a double bond.

Preferred estrenes include 1,3,5(10)-Estratriene-3, 17β-diol; 1,3,5(10)-Estratriene-3,16α, 17β-triol; 1,3,5(10)-Estratriene-3-ol-17-one; 1,3,5(10),16-Estratetraen-3-ol; 1,3,5 (10),16-Estratetraen-3-ol methyl ether; and 1,3,5(10), 16-Estratetraen-3-yl acetate.

Most of these steroids and their glucuronide, sulfate, cypionate, and benzoate derivatives, are compounds known in the art and are commercially available, e.g., from Sigma Chemical Co., Aldrich Chemical Co., etc. Alkoxy derivatives and their syntheses are also known in the art and shown in U.S. Pat. No. 2,984,677.

1,3,5(10),16-Estratetraen-3-ol is available from Research Plus, Inc. and from Steraloids, Inc. Another synthesis of this compound, as well as syntheses of the acetate and propionate derivatives are described in the commonly assigned, co-pending continuation-in-part of U.S. Ser. No. 07/903,525, which is in turn a continuation-in-part of U.S. Ser. No. 07/707,862, incorporated herein by reference.

C. Synthetic Methods

1. Preparation of 3-, 5-, 6-, 18- and 19-position derivatives.

The compounds used in the methods of this invention are Androstane steroids substituted at the 3-, 5-, 6-, 18- and 19-positions. Many of the 3-and 5-substituted steroids are known compounds which may be derived from 17-hydroxy- and 17-oxo-steroids (commercially available e.g. from Aldrich Chemical Co) by elimination or reduction to the Δ16 homologue. The syntheses of most of these compounds are described by Ohloff (supra). As shown in FIG. 1, 17β-hydroxy-5α-Androstan-3-one (I) and methyl chloroformate (a) in pyridine gives the methyl carbonate, 17β-methoxycarbonyloxy-5α-Androstan-3-one (II) which provides a starting material for the 5α-Androst-16-en-(3-one and 3-ols) (Ohloff, supra at pg 200).

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aprotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the work-up procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

2. Preparation of 19-OH derivatives

Synthesis of 19-OH-Androsta-4,16-diene-3-one

This compound has been disclosed as an intermediate in the synthesis of 19-oxo-3-aza-A-homo-5B-androstane (Habermehl, et al., Z. Naturforsch, (1970) 25b:191–195). A method of synthesizing this compound is provided.

D. Pharmaceutical Compositions and Methods of Use

An embodiment of the subject invention is a method of altering the hypothalamic function of an individual. Another embodiment is altering an autonomic function of an individual. These autonomic functions include but are not limited to heart rate, respiratory rate, brain wave patterns (percentage alpha cortical activity), body temperature. Other embodiments include, but are not limited to, methods of diminishing negative affect, negative mood or negative character traits of an individual. Another embodiment is a method of treating female premenstrual stress. All of these embodiments are accomplished by means of the non-systemic, nasal administration of certain 16-Androstene steroids, combinations of 16-Androstene steroids and combinations of one or more 16-Androstene steroids and one or more Estrene steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., non-invasively. Drug action is mediated through binding of the ligands, described herein, to specific receptors displayed by neuroepithelial cells in the nose, preferably in the VNO. This Furthermore, the mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary (See Johnson, et al., supra).

The ligand substances described herein, or their sulfated, cypionated, benzoated, proprionated, or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol. Alternatively, the active compound can be prepared as a creme or an ointment composition and applied topically within the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active 16-Androstene compound(s) of Formula I, and the composition may or may not additionally include one or more Estrene steroids. In addition, the compositions may include other medicinal agents, pharmaceutical agents, carriers, adjuvants, etc.

The most likely means of communication of a semiochemical ligand is the inhalation of a naturally occurring pheromone present on the skin of another. Several 16-Androstene steroids, including 5α-Androst-16-en-3α-ol and 5α-Androst-16-en-3-one, 4, 16-Androstadien-3-one, 5α-Androstadien-3β-ol, and perhaps 5α-Androstadien-3α-ol, are naturally occurring in humans and may be present on the skin. It is estimated that the naturally occurring maximum concentration of a 16-Androstene steroid on human skin is from 2 to 7 ng/cm$^2$. During intimate contact it is estimated that a human would be exposed to no more than 700 ng of a naturally occurring steroid. Since these compounds are relatively nonvolatile, it is estimated that, even during intimate contact, a human subject would inhale no more than 0.7 pg of a naturally occurring steroid from the skin of another.

From the amount inhaled only about 1% would reach the receptors of the vomeronasal organ. Thus the estimated maximum natural exposure to naturally produced pheromones would be 0.007 pg.

The amount of semiochemical ligand administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response. When administered to the nasal cavity, the dosage is about 100 picograms to about 100 micrograms, preferably about 1 nanogram to about 10 micrograms, more preferably about 10 nanograms to 1 about microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Co., Easton, Pa., 15th Ed., 1975. The composition or formulation to be administered will, in any event, contain a quantity of one or more of the active compounds() in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant.

Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monoleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

F. Measuring Affect. Mood and Character Trait.

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of related adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp. 1417. In: Medical Physiology. Vol. IIEd.:VB Mountcastle (1980); Wolfram Bouscein. Electrodermal Activity (Plenum Press 1992). In addition, non-verbal cues such as facial expression and body posture may be evaluated.

III. EXAMPLES

The following examples are intended to illustrate but not to limit the invention.

Abbreviations used in the examples are as follows:aq.
aqueous; RT.=room temperature; PE=petroleum ether (b.p. 50–700); DMF=N,N-dimethylformamide; DMSO=dimethyl sulfoxide; THF=tetrahydrofuran.

Example 1

Androsta-4,16-dien-3-one (4)

This synthesis is depicted in FIG. 1. Several methods are known for the conversion of testosterone into Androsta-4, 16-dien-3-one (Brooksbank et al, *Biochem. J.* (1950) AZ:36). Alternatively, thermolysis (460°) of the methyl carbonate of testosterone gives Androsta-4,16-dien-3-one in 90% yield. 17B-MethoxyCarbonyioxy-androst-4-en-3-one (IV) was prepared from testosterone (III. Fluka) with methyl chloroformate/pyridine (a) in 76% yield (after recrystallization from MeOH). M.p. 140–141°, $[a]_D$=+95.4°(c=1.10) IR. $(CDCl_3)$:1740s, 1665s, 1450s, 1280s, $^1$H-NMR. (360 MHz) :0.87 (s, 3H); 1.20 (s, 3H); 3.77 (s, 3H); 4.53 (br. t, J 8, 1H); 5.75 (s, 1H). A solution of the methyl carbonate IV in toluene was pyrolyzed (b) as described for I. Recrystallization of the crude product from acetone at RT. gave pure ketone 4 in 90% yield. M.p. 127–129.5°, $(a)_D$+118.90°(C= 1.32) ([3]:m.p. 131.5–133.5°(hexane), $[a]_D^{16}$=+123±3.50° (C=1.03)). IR. $(CDCl_3)$:3050w, 1660s, 1615m. $^1$H-NMR. (360 MHz):0.82 (s, 3H); 1.22 (s, 3H); 5.70 (m, 1H); 5.73 (s, 1H); 5.84 (m, 1H).

Example 2

Androsta-4,16-dien-3α-ol (5) and -3β-ol (6)

These syntheses are depicted in FIG. 1. Androsta-4,16-dien-3-one (4) was reduced at −55° with lithium tris (1, 2-dimethylpropyl) hydridoborate in THF (c) as described for the preparation of 2 (FIG. 1). Chromatography on silica gel with $CH_2Cl_2$/ethyl acetate 9:1 gave pure axial alcohol 5 (48% yield) and pure equatorial alcohol 6 (48% yield). Analytical samples were further purified by recrystallization (from PE at −30° for 5, from cyclohexane at RT. for 6).

Data of 5. M.p. 77–790, $[a]_D$+120.60° (C=1.26) IR. $(CDCl_3)$:3620m, 3440m br., 1660m, 1595w. $^1$H-NMR. (360 MHz):0.79 (s, 3H); 1.02 (s, 3H); 4.07 (m, $w_{1/2}$≈10, 1H); 5.48 (d×d, J 5 and 2, 1H); 5.71 (m, 1H); 5.85 (m, 1H).

Data of 6. M.p. 116.1190, $[a]_D$+53.9° (C=1.28) ([47]:m.p. 116.1180, $[^8)D$ +59.3° (C=0.4) IR. $(CDCl_3)$:3610m, 3420m br., 3050m, 1660m, 1590w. $^1$H-NMR. (360 MHz):0.78 (s, 3H); 1.08 (s, 3H); 4.15 (m, $w_{1/2}$ ≈20, 1H); 5.30 (m, w½ ≈5, 1H); 5.71 (m, 1H); 5.85 (m, 1H)

Example 3

Androsta-5,16-dien-3α-ol (7)

Figure 2:
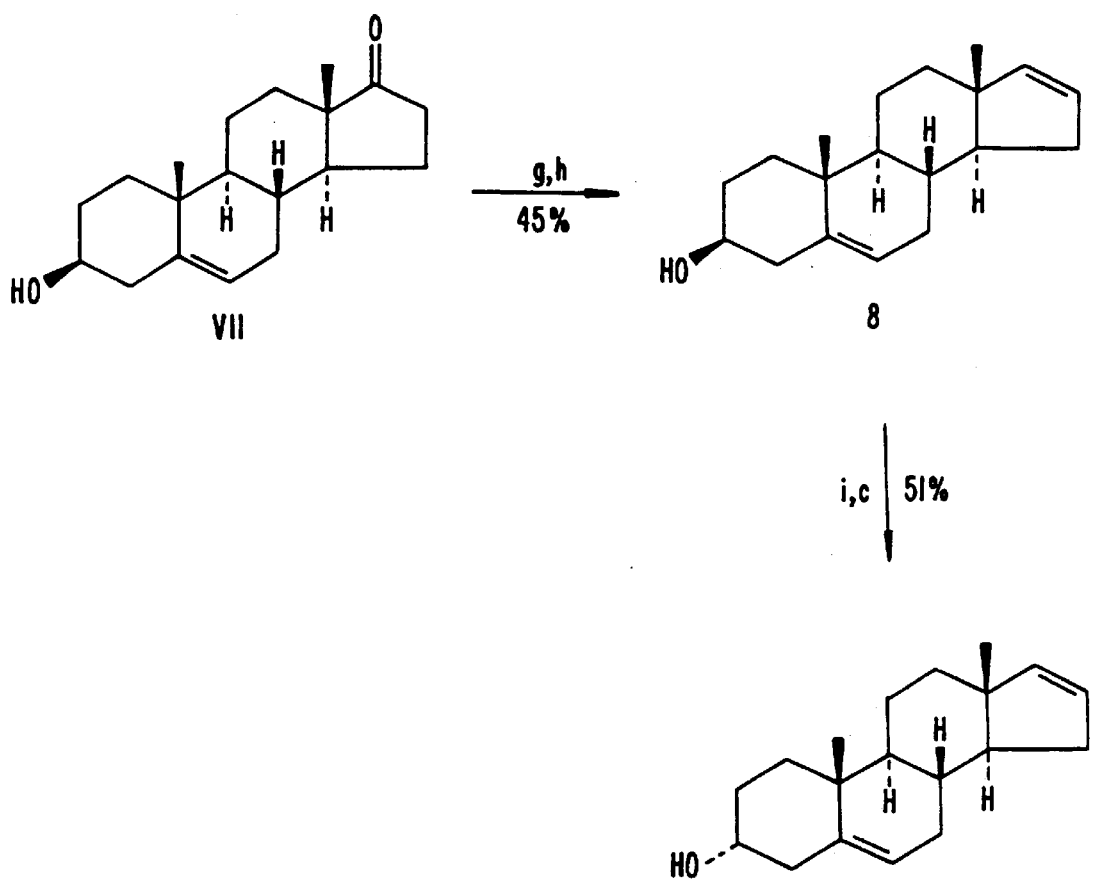
FIG. 2 illustrates the synthesis of Androsta-5,16-dien-3α-ol and Androsta-5,16-dien-3β-ol.

This synthesis is depicted in FIG. 2. To a solution of alcohol 8 (545 mg, 2.0 mmol) in acetone (100 ml) at 0° C. under $N_2$was added rapidly Jones reagent (i, 1.5 ml, ca. 4 mmol). After 5 min., the mixture was poured into a dilute phosphate buffer (pH 7.2, 1200 ml) and extracted with ether. The extracts were washed with sat. aq. NaCl solution, dried $(Na_2SO_4)$ and evaporated to give mainly Androsta-5,16-dien-3-one as an oil (567 mg). The crude product was dissolved In THF (7 ml) and reduced with lithium tris (1,2-dimethylpropyl) hydridoborate (c) at 0.55° as described for the preparation of 2. The crude product (530 mg) was chromatographed on silica gel (100 g) with $CH_2Cl_2$/ethyl acetate 4:1 to give 280 mg (51%) of pure a-alcohol 7 (eluted first) and 13 mg of starting alcohol 8. A small sample of 7 was recrystallized from acetone/water at RT. M.p. 1380, $[^8]D$ −77.5° (c=2. IR. $(CDCl_3)$:3580m, 3430m, 1665w, 1590w, $^1$H-NMR. (360 MHz):0.80 (s, 3H); 1.06 (s, 3H); 4.02 (m, w½≈8, 1H); 5.44 (m, 1H); 5.72 (m, 1H); 5.86 (m, 1H).

Example 4

Androsta-5,16-dien-3B-ol (8)

This compound was prepared in 73% yield by a known procedure (Marx, A. F., et al., Ger. Offen. 2,631,915; Chem. Abst. 87:23614p (1977)) from commercial (Fluka) 3B-hydroxy-androst-5-en-17-one (VII). M.p. 137°, $[a]_D$=− 71.9° (c=1.5) ([48]:m.p. 140–141°, $[a]_D$=68°. IR. $(CDCl_3)$ :3600m, 3420m br., 1670w, 1590w, $^1$H-NMR. (360 MHz) :0.80 (s, 3 H); 1.05 (s, 3H); 3.53 (m, $w_{1/2}$≈22, 1H); 5.38 (m, 1H); 5.72 (m, 1H); 5.86 (m, 1H). This synthesis is depicted in FIG. 4.

Example 5

Alternate synthesis of Androsta-4,16-dien-3-one (25)

Figure 3:
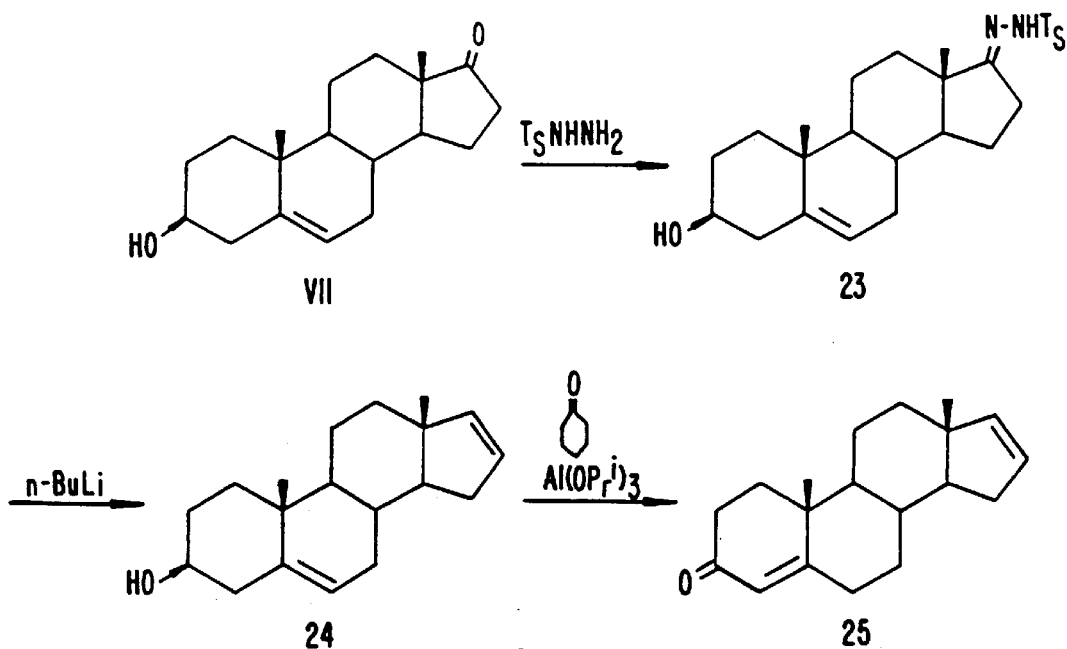
FIG. 3 illustrates an alternate synthesis of Androsta-4,16-dien-3-one.

The following method of synthesis is depicted in FIG. 3: Dehydroepiandrosterone p-Toluenesulfonylhydrazone (23)

Dehydroepiandrosterone (VII) (14.4 g, 50.0 m mole) and p-toluenesulfonylhydrazide (12.75 g, 68.5 m mole) in dry methanol (300 ml) were heated under reflux for 20 hours. The mixture was transferred to a conical flask and allowed to cool. The crystalline product was filtered under suction and washed with methanol (50 ml). Further crops of product were obtained by sequentially evaporating the filtrate to 75 ml and 20 ml, and allowing crystallization each time. Total yield was 21.6 g (95%).

Androsta-5, 16-dien-3β-ol (24)

Dehydroepiandrosterone p-toluenesulfonylhydrazone (23) (22.8g, 50.0 m mole) in dry tetrahydrofuran (1.0 liters) was cooled in a dry ice/isopropanol bath, The mixture was stirred while n-butyl lithium (125 ml of 1.6 M solution in hexane, 200 m mole) was added. The mixture was allowed to warm to room temperature and was stirred for 24 hours. Water (50 ml) was added with cooling in ice. The mixture was poured into saturated ammonium chloride solution/ice (500 ml) and extracted with ether (x2). The organic layers were washed with saturated sodium bicarbonate solution (500 ml) and saturated sodium chloride solution (500 ml), dried ($MgSO_4$) and evaporated in vacuo to give the crude product. This was purified by flash chromatography on 190 g silica gel 60, 230–400 mesh, eluting with ethyl acetate/hexane (20:80→50:50) to give crystalline material. The product was recrystallized from methanol (45 ml)/3% hydrogen peroxide -(8 ml) washing with methanol (30 ml)/water (8 ml) to give pure product (6.75 g, 50%).

Androsta-4, 16-dien-3-one (25)

A solution of 10 g of Androsta-5,16-dien-3β-ol (24) in 475 cc of toluene and 75 cc of cyclohexanone was distilled (ca. 50 cc of distillate was collected) to eliminate moisture, 5 g of $Al(OPr^i)_3$ in 50 cc of toluene was added and the solution was refluxed for 1 hour. Water then was added, volatile components were removed by steam distillation and the residue was extracted with chloroform. Evaporation of the dried extract, followed by crystallization of the residue from chloroform-hexane, yielded 7.53 g of Androsta-4,16-dien-3-one (25). Another 0.97 g (total, 8.5 g, 86%) was obtained by chromatography of the mother liquor on neutral alumina.

Example 6

Synthesis of Androsta-3,5,16-trien-3-yl methyl ether (12)

To a partial solution of androsta-4,16-dien-3-one (1.00 g, 3.70 mmol) in 2.2-dimethoxypropane (5.0 mL, 41 mmol) and 5 mL DMF were added methanol (0.2 mL) and p-toluenesulfonic acid monohydrate (26.4 mg, 0.139 mmol). The mixture was refluxed 5 h, after which it was cooled and sodium bicarbonate (152.5 mg) was added. The suspension was partitioned between 50 mL of ice water and 50 mL of ethyl acetate. The organic layer was washed with two 50 mL portions of water+50 mL of brine, dried over magnesium sulfate, filtered, and concentrated under reduced pressure. The residual oil was taken up in 50 mL of hot hexane and filtered through a 12 mm×30 mm column of silica gel 60 using 150 mL of hot hexane. The combined filtrates were concentrated under reduced pressure and recrystallized from acetone/methanol to give white crystals (468.0 mg, 1.645 mmol, 44%), m.p. 83–92° C.

Example 7

Synthesis of 17-methylene-Androst-4-en-ols

To 20-homoandrosta-4,17-dien-3-one (119.0 mg, 0.4184 mmol) in 5 mL of methanol were added sodium borohydride (6.0 mg, 0.16 mmol) and 77 μL of water. After stirring 2 h further sodium borohydride (32.0 mg, 0.846 mmol) was added and the mixture was stirred overnight. After concentrating under reduced pressure the residue was purified by preparative TLC (5% ethyl acetate/hexane on silica gel) to give a more polar (59.8 mg) and a less polar (1.7 mg) product.

Example 8

Synthesis of 17-methylene-6-oxo-Androsta-4-en-3-one

To a cooled solution of 20-homoandrosta-5,17-dien-3-ol (399.4 mg, 1.394 mmol) in 50 mL of acetone was added 2.67M Jones reagent (2.0 mL, 5.3 mmol). After stirring 1 h the reaction was quenched with isopropanol (1.0 mL, 13 mmol) and poured into 100 mL of water. The mixture was extracted three times with 50 mL portions of ethyl acetate and the combined organic extracts were washed with 50 mL of saturated sodium bicarbonate +50 mL of brine. The organic phase was then dried over magnesium sulfate, filtered, and concentrated under reduced pressure. The residue was recrystallized from 95% ethanol to give an almost white powder (177.8 mg, 0.5958 mmol, 43%), m.p. 113–115° C.

Example 9

Synthesis of 6β-OH-Androsta-4,16-dien-3-one

To a solution of androsta-3,5,16-trien-3-yl methyl ether, (12) (200.5 mg, 0.7049 mmol), in 5 mL of 1,2-dimethoxyethane (DME) and 1 mL of water was added m-chloroperbenzoic acid (MCPBA, 77.4%, 173.2 mg, 0.776 mmol) suspended in 5 mL of DME+1 mL of water+0.40 g of 5% (w/w) NaOH dropwise, with stirring, over a period of 90 min. After stirring 18 h further MCPBA (247.0 mg, 1.11 mmol) suspended in 10 mL of DME+2 mL of water+0.8 g of 5% (w/w) NaOH was added dropwise, with stirring, over 1½ h. The reaction mixture was stirred ½ h and then poured into 25 mL of saturated sodium bicarbonate. The aqueous mixture was extracted three times with 25 mL of ether and the combined organic extracts were washed with 50 g of 5% (w/w) sodium thiosulfate+three 50 mL portions of brine, dried over magnesium sulfate, filtered through Celite, and concentrated under reduced pressure. The resulting crystalline residue was purified by preparative TLC (35% ethyl acetate/hexane on silica gel) followed by two-fold recrystallization from aqueous ethanol to give lustrous white platelets (102.3 mg, 0.3571 mmol, 51%), m.p. 165–166° C.

Example 10

Electrophysiology of Androstane Stimulation of the Human VNO and Olfactory Epithelium A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. This electrode and delivery system has been described by Monti and Grosser (*J. Steroid Biochem. and Molec. Biol.* (1991) 39:573) and in commonly owned, copending U.S. Ser. No 07/771,414, incorporated herein by reference. The local response of the VNO and the OE showed a correlation with the concentration of the ligand stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specule) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, nonodorous, humidified air at room temperature was continuously passed through a channel of the stimulating system. The stimulating ligand substances were diluted in propylene glycol, mixed with the humidified air, and puffed for from 1 to 2 seconds through the catheter/electrode. It is estimated that this administration provides about 25 pg of the steroid-ligand to the nasal cavity.

Figure 4A:
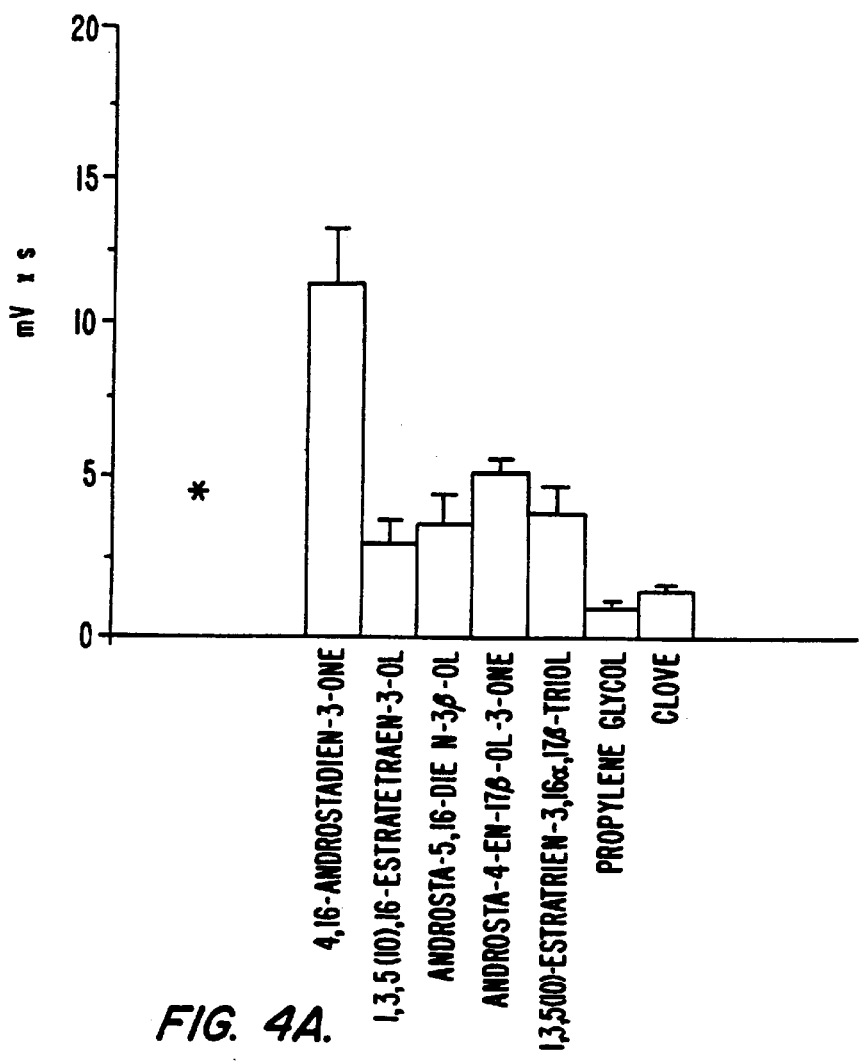
FIG. 4 is a graphic representation of the electrophysiological effect on receptor potential of the localized administration of particular steroids to the vomeronasal organ of female subjects (4A) and to the olfactory epithelium (4C).
FIG. 4B is a graphic comparison of the effect of an Androstane on the VNO receptor potential of male and female subjects.
Figure 4B:
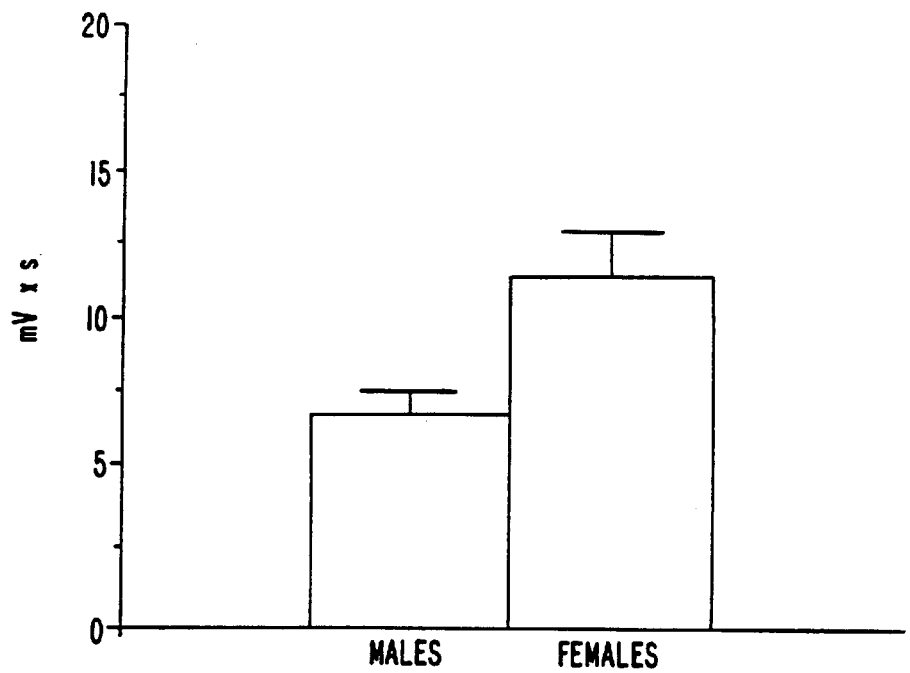
Figure 4C:
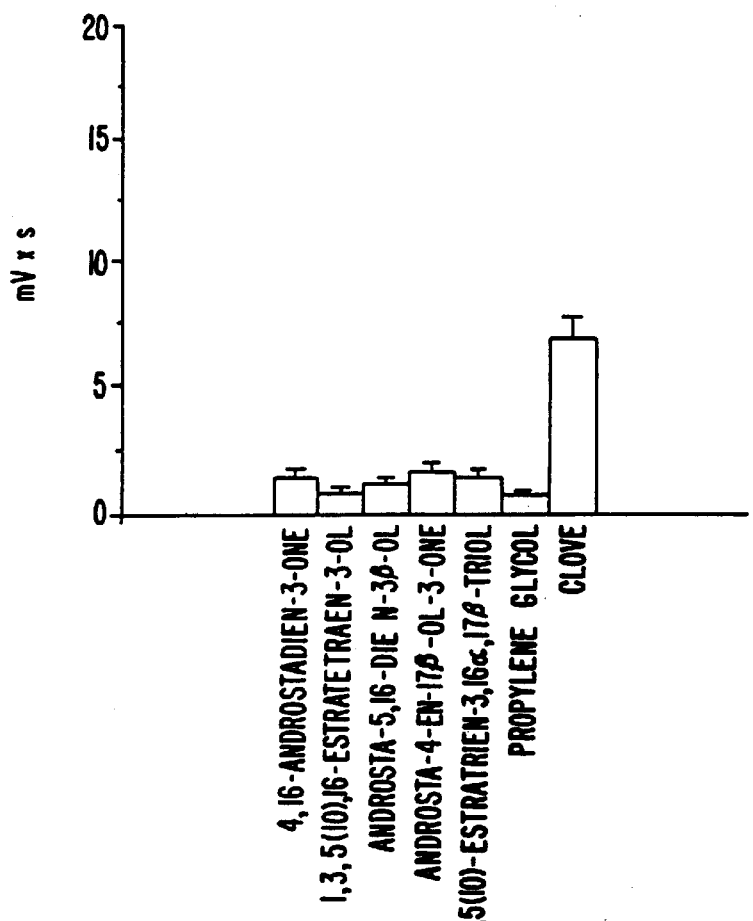

The results of this study are presented in FIGS. 4A, 4B, and 4C. The response is measured in millivolt-seconds (mV×s). Androsta-4,16-dien-3-one elicits a significantly stronger VNO response in females than do the other compounds tested (FIG. 4A). Furthermore, the VNO response to Androsta-4,16-dien-3-one is sexually dimorphic—twice as strong in females as it is in males (FIG. 4B). In contrast, the OE response in both males and females is low compared to a strong odorant such as clove (FIG. 4C).

Example 11

Figure 5A:
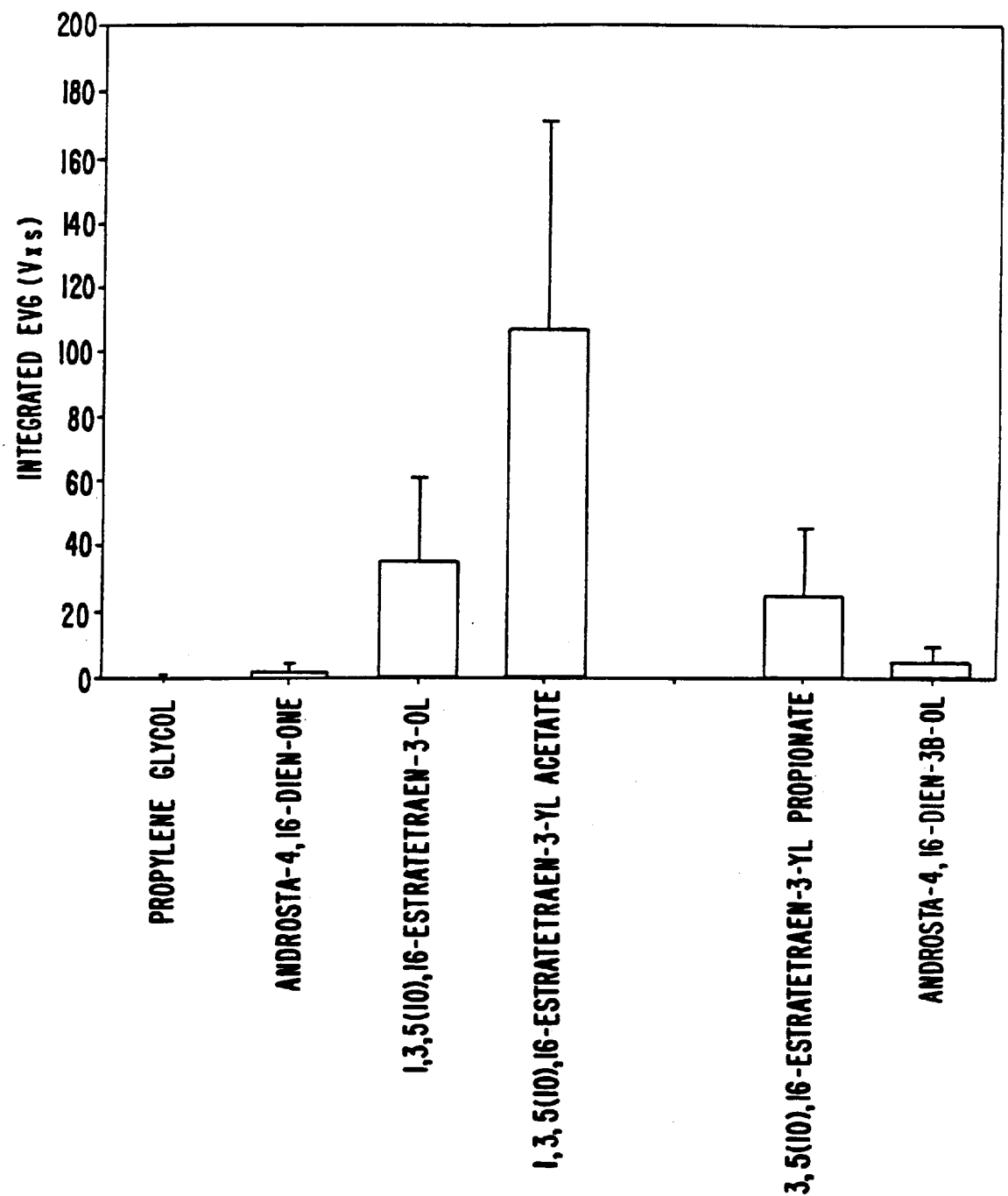
FIG. 5 is a graphic representation of the electrophysiological effect of the localized administration of particular steroids to the vomeronasal organ of male (5A) and female (5B) subjects.
Figure 5B:
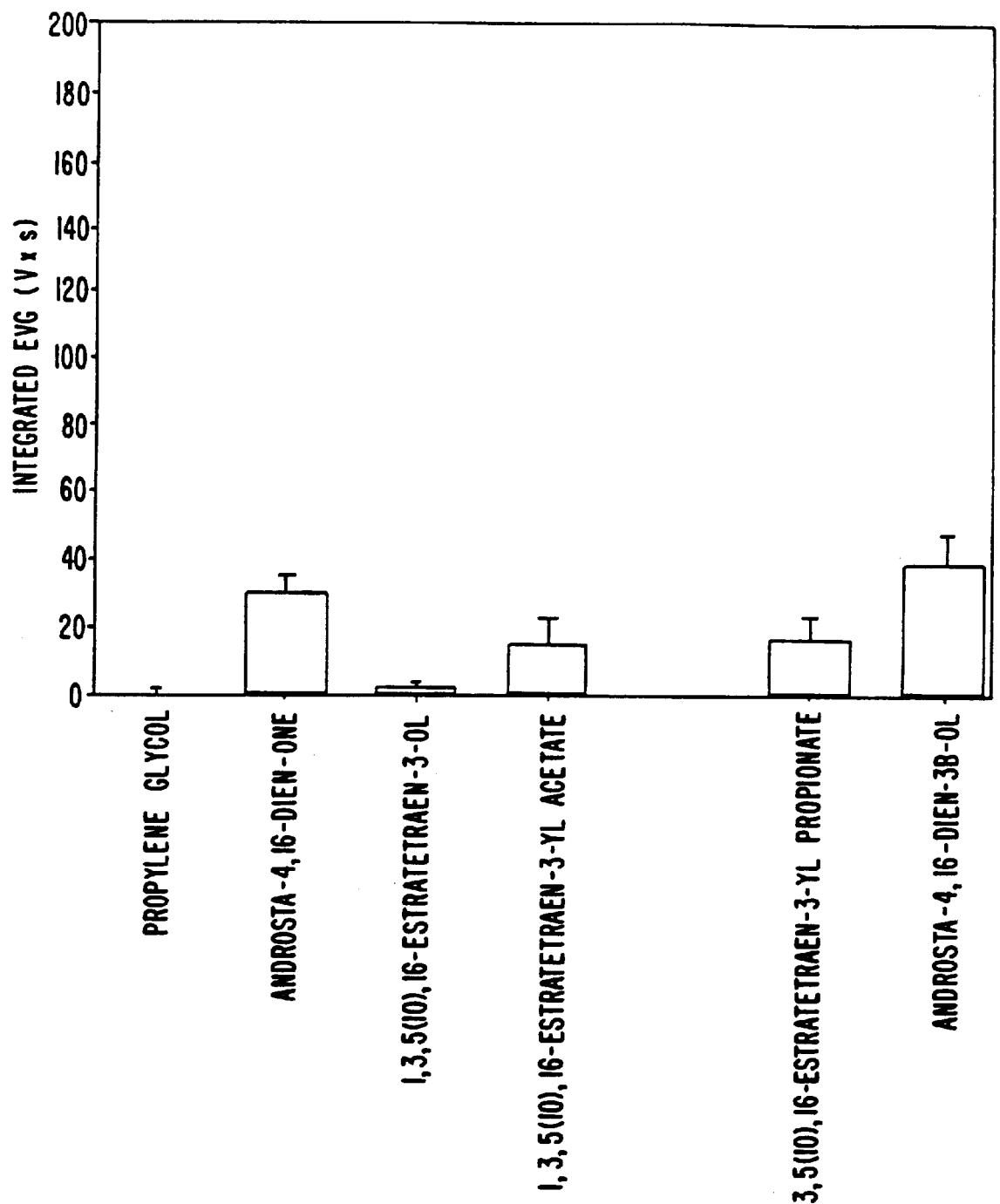
Figure 6A:
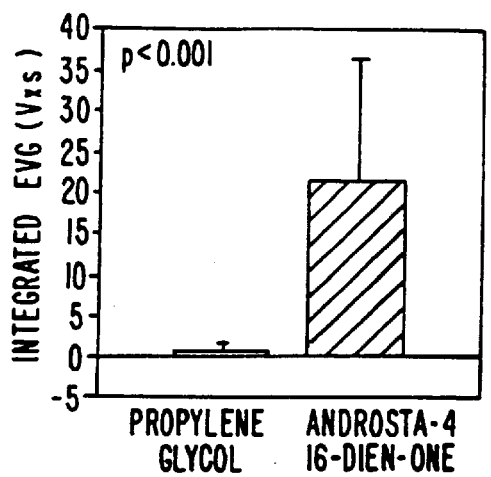
FIG. 6 depicts various autonomic responses of female subjects to an Androstane. A=receptor potential of the vomeronasal neuroepithelium; B=change in cortical alpha activity of an electroencephalogram (%); C=change in galvanic skin response (K-ohms); D=change in peripheral arterial pulse (counts/min.); E=change in skin temperature (degrees C.); and, F=change in respiratory frequency (counts/min.).
Figure 6B:
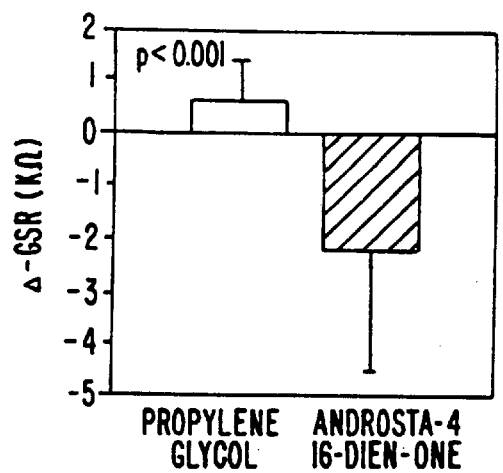
Figure 6C:
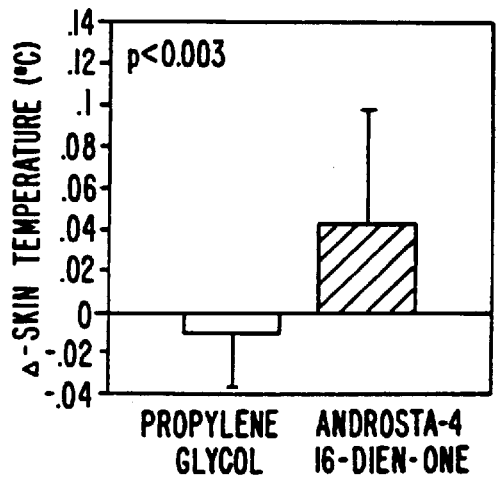
Figure 6D:
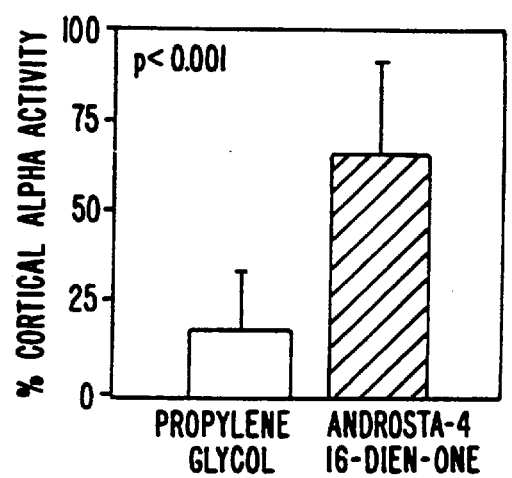
Figure 6E:
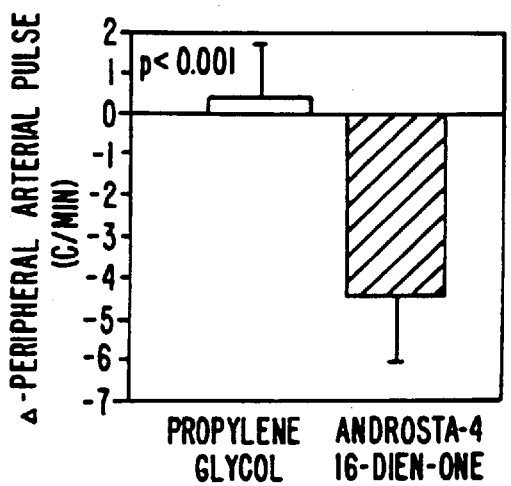
Figure 6F:
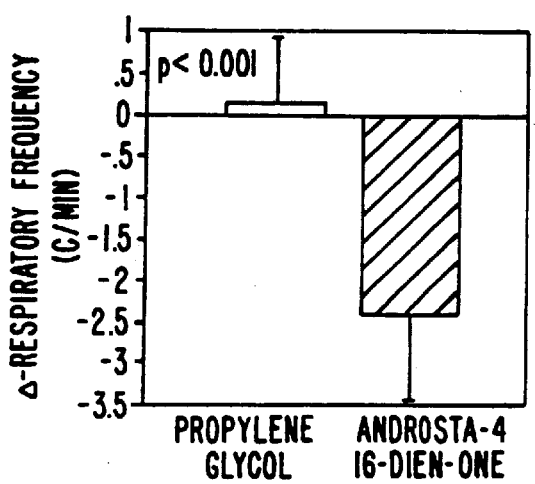

Measurement of the Change in Receptor Potential of the Neuroepitihelium of the VNO in Response to Various Steroids The change in receptor potential in response to five different ligands was measured in 40 female (FIG. 5A) and 40 male (FIG. 5B) subjects. Each subject was administered 60 pg of each of seven substances as indicated in the figure. The substances were administered separately for 1 second, using the procedure described in Example 10. The change in potential of the neuroepithelium of the VNO was recorded over time and the integral of the change in potential for each of the forty subjects was averaged. The results are shown in the figure. Comparison of FIGS. 5A and 5B show that each steroid is sexually dimorphic in its activity, and that some ligand substances are stronger in males while others are stronger in females.

Example 12

Measurement of Autonomic Responses to 16-Androstene Stimulation of the VNO

Various autonomic parameters were monitored as Androsta-4,16-dien-3-one was administered to 40 female subjects using the procedure described in Example 10. Propylene glycol was also administered as a control. The ligand was administered as a 1 second pulse. The change in autonomic function was first noted within 2 seconds and lasted for up to 45 seconds. As shown in FIG. 6, when compared to a propylene glycol control, the Androstane induced a significant change in the integrated receptor potential in the VNO (6A), galvanic skin response (6B), skin temperature (6C), the percentage of cortical alpha wave activity as measured by electroencephalogram (6D), peripheral arterial pulse (6E), and respiratory frequency (6F).

Example 13

Figure 7:
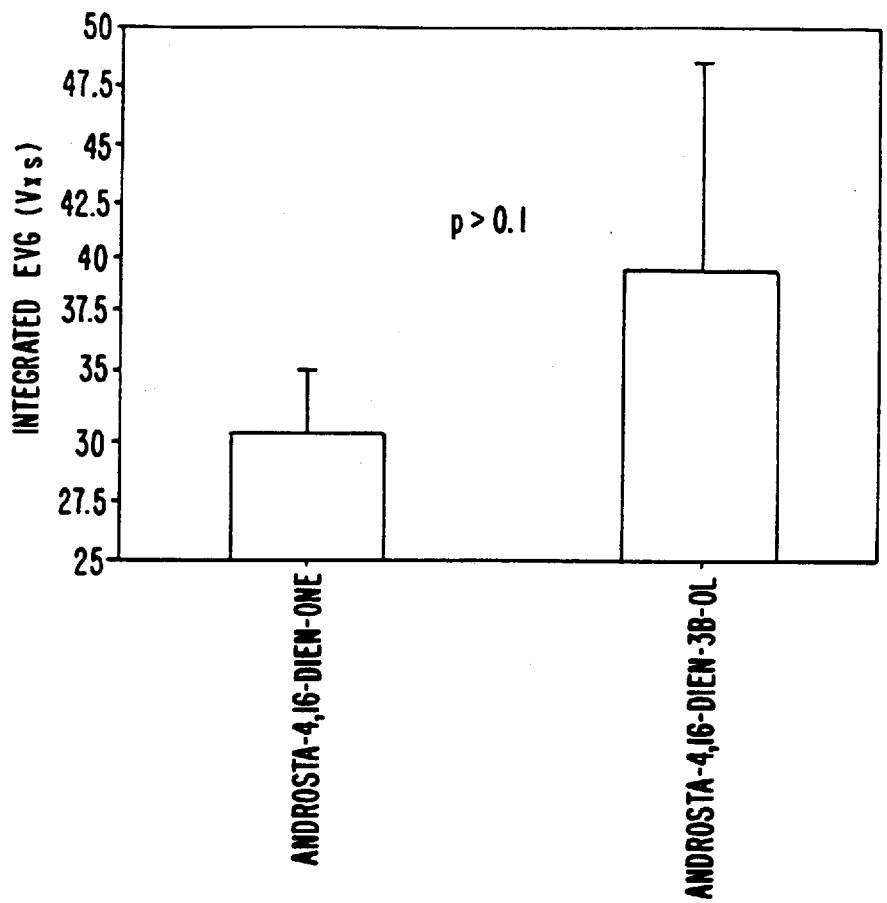
FIG. 7 depicts changes in receptor potential of the VNO after exposure of 5 females to two different Androstanes.

Comparison of the Change in Receptor Potential Induced by Two Androstane Steroids 60 picograms of each ligand steroid and of a propylene glycol control were administered to 5 female subjects as described in Example 10. As shown in FIG. 7, Androsta-4, 16-dien-3β-ol induced a greater change in receptor potential than did Androsta-4,16-dien-3-one.

Example 14

Psychophysiological Effect of Androstane Stimulation of the VNO

The psychophysiological effect of Androstane stimulation of the VNO was measured by the coordinate administration of pheromone and questionnaire evaluation of the subject before and after administration. The questionnaire included a panel of adjectives used as part of the standard Derogatis Sexual Inventory evaluation.

The subjects were 40 women between the ages of 20 and 45, all in good health. The women were randomly assigned—20 exposed to placebo and 20 exposed to about 20 picograms of Androsta-4,16-dien-3-one, administered as described in Example 10, supra. Subjects were given a 70 item questionnaire evaluating feeling states immediately before and 30 minutes after administration of either placebo or experimental substance. The 70 adjectives of the questionnaire were randomly administered and subsequently clustered for evaluation based on their relevance to each mood, feeling, or character trait. The results were as follows:Changes in feelings of social warmth, personal well-being, arousal/excitement, and aggression, from before administration to 30 minutes after administration, were not significant in those exposed to the 16-Androstene compared to the changes resulting from administration of the control. However, the decrease in negative affect (nervous, tense, ashamed, anxious, irritable, angry, enraged—T-test:$p<0.0001$, Anova: $p<0.04$), negative mood and character (sensitive, regretful, blameworthy, guilty, remorseful, sad, hopeless, resentful, worthless, miserable, unhappy, bitter, timid—T-test:$p<0.0004$, Anova:$p<0.06$), and overall negativity (the combination of affect and character–T-test:$p<0.0003$, Anova:$p<0.05$) were highly significant after 16-Androstene administration as compared to administration of the control.

Overall, these results suggest a sedative and/or anti-anxiety, and/or anti-depressant effect of Androsta-4,16-dien-3-one when administered intranasally.

Example 15

Treatment of Women for Premenstrual Stress

Women experiencing the symptoms of premenstrual stress (PMS) are provided with a pharmaceutical preparation of an Androstane steroid (preferably Androsta-4,16-dien-3-one, or Androsta-4, 16-dien-3α(β)-ol) suitable for nasal administration. The steroid is provided as an ointment at a concentration of about 1 microgram/ml and about 0.1 ml is applied. The ointment is applied just inside the nare of each nostril, three times daily. A similar method of treating PMS uses an aerosol preparation of the same steroid. The aerosol is sprayed into each nostril threes times daily.

Example 16

Electrophysiological Studies

The following electrophysiological studies were performed in 60 clinically normal human volunteers of both sexes (30 male and 30 female) whose ages ranged from 20 to 45 years. No anesthetics were used, and female subjects were excluded if pregnant.

The stimulation and recording system consists of a "multifunctional miniprobe" described elsewhere (Monti-Bloch, L. and Grosser, B. 1. (1991) "Effect of putative pheromones on the electrical activity of the human vomeronasal organ and olfactory epithelium," *J. Steroid Biochem. Molec. Biol.* 3:573–582.). The recording electrode is a 0.3 mm silver ball attached to a small (0.1 mm) silver wire insulated with Teflon the surface of the electrode is first treated to produce a silver chloride interface, and is then covered with gelatin It is positioned within a small caliber Teflon catheter (dia=5 mm) such that the tip of the electrode protrudes approximately 2 mm. The Teflon catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon tube with a diameter of 2 mm surrounds the catheter-electrode assemblage, and its central end is connected to an aspirator that provides continuous suction of 3ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNO, or on the surface of the olfactory or respiratory epithelium.

Electro-vomeronasogram (EVG) Recordings are carried out in a quiet room with the subject supine; the multi-functional miniprobe is initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6x magnifying binocular loupe with halogen illumination is then used to introduce the tip of the Teflon® catheter and recording electrode assemblage into the VNO opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. Artifacts produced by respiratory movements are deleted by training the subjects to practice mouth breathing with velopharyngeal closure.

Chemosensory Stimulants

Olfactory test substances are cineole, and 1-carvone; vomeropherins are A, B, C, D, E and F. Samples of vomeropherins in concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon©, glass or stainless steel and are carefully cleaned and sterilized before each use.

Electro-olfactgram (EOG)

Olfactory recordings employed the same stimulating and recording multifunctional miniprobe as that used for the VNO. The tip was slowly introduced until the recording electrode touched the olfactory mucosa. Adequate placement was signaled by a depolarization in response to a pulse of the odorant test substance.

Cortical evoked activity was induced by VNO stimulation with vomeropherins, and olfactory stimulation with odorants delivered in 300 ms air pulses. It was recorded using standard electroencephalographic (EEG) electrodes placed at positions Cz-A1 and Tz-A1 of the international 10120 system; the ground electrode was placed on the mastoid process. Electrodermal activity (EDA) was recorded using standard 8 mm silver electrodes in contact with palmar skin of the medial and ring fingers respectively, through a conductive gel interface. Skin temperature (ST) was recorded by a small (1.0 mm) thermistor probe placed in the right ear lobe. Peripheral arterial pulse (PAP) was monitored with a plethysmograph attached to the tip of the index finger. Respiratory frequency (RF) was measured with an adjustable strain gauge placed around the lower thorax. All electrical signals were DC amplified, digitized (MP-100, Biopac Systems) and continuously monitored utilizing a computer.

Statistical Analysis

EVGs or EOGS, peak-to-peak changes and frequency changes of other parameters were measured and statistically analyzed. The significance of the results was determined by either using paired t-tests or analysis of variance (ANOVA).

Effect of Vomeropherins on the EVG

Figure 8A:
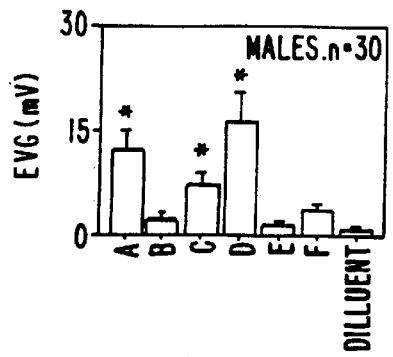
FIGS. 8A & B: EVG responses were measured as described in male (A) and female (B) subjects.
Figure 8B:
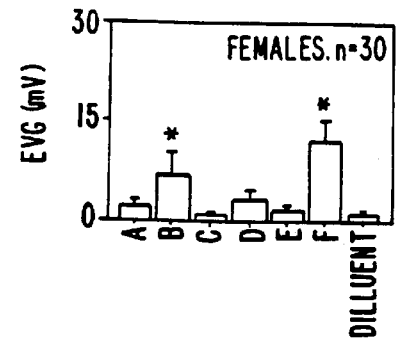
FIG. 8 depicts sexual dimorphism in local and autonomic responses to the stimulation of the VNO with vomeropherins. Various vomeropherins (200 fmoles) and the diluent control were administered to 30 male and 30 female subjects (ages 20 to 45) as described. Bars indicate the mean response of the population.
FIGS. 8C & D: Electrodermal activity was measured as described. Changes (measured in xΩ) in response due to delivery of vomeropherins to the VNO of each subject are shown in male (C) and female (D) subjects.
FIGS. 8E & F: Alpha-cortical activity was measured as described. Changes in response due to delivery of vomeropherins to the VNO of male (E) and female (F) subjects.
FIGS. 8G & H: Skin temperature (ST) wad measured as described. Changes in response due to delivery of vomeropherins to the VNO of each subject are shown in male (G) and female (H) subjects.
Figure 8C:
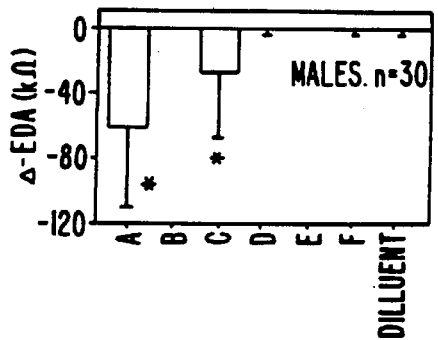
Figure 8D:
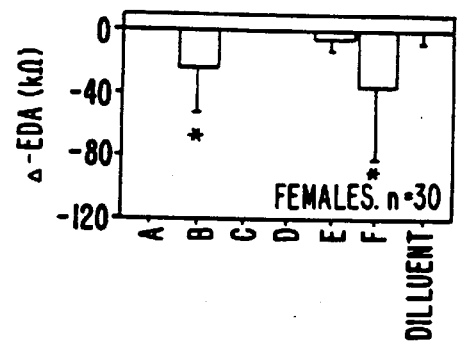
Figure 8E:
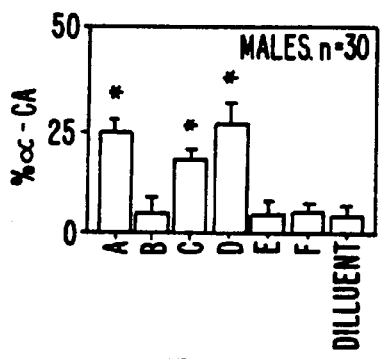
Figure 8F:
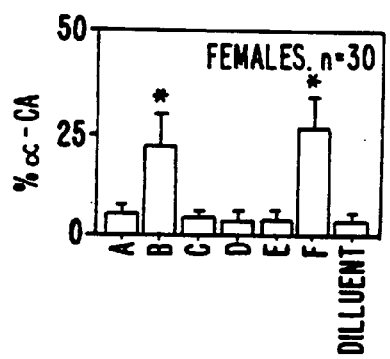

Each of the vomeropherins was found to produce a sexually dimorphic receptor potential (FIG. 8A–B). Recordings of the EVG were performed on 30 men and 30 women (ages 20 to 45). Vomeropherins were diluted and applied as 1 second pulses to the VNO with b minute intervals between pulses when questioned, the subjects were not able to "smell" or otherwise consciously detect any of the vomeropherins. This finding is in agreement with results previously reported (Monti-Bloch, L. and Grosser, B. 1. (1991) "Effect of putative pheromones on the electrical activity of the human vomeronasal organ and olfactory epithelium," *J. Steroid Biochem. Molec. Biol.* 23:573–582.) which indicated that neither olfactory nor vomeropherin test stimuli delivered to the VNO elicit a perceptible sensation at the delivered concentration.

FIG. 8A shows the average response of male subjects (ages 20 to 38) to the diluent, and to equimolar quantities (100 fmoles) of five vomeropherins (A, B, C, D and F), and to E, a stereoisomer of F. The profile of the response to each of the substances was similar in all subjects regardless of age, and no significant differences were revealed either by t-tests or by analysis of variance. For example, A, C and D produced significant effects ($M_{15}$=11.4 mV, SD=3.6 mV; $M_{76}$=6.4 mV, SD 2.5 mV, and $M_{84}$=15.1 mV, SD=4.9mV; $p<0.01$), that were consistent in all individual cases. Other vomeropherins depolarized the VNO-receptors to a much lesser extent, but with consistent mean response amplitudes from individual to individual. Vomeropherins active in male subjects produced larger responses than the diluent ($p<0.001$). B, F and similar concentrations of olfactants induced significantly reduced responses in the male VNO (FIG. 8A and FIG. 9).

A similar experimental protocol was followed with the 30 female subjects (ages 20–45). Among the vomeropherins, F (100 fmoles) produced the most significant differences within the group (FIG. 8B). Here, A induced a small effect that was significantly different from F ($p<0.01$). In both populations of subjects, active vomeropherins induced receptor responses having large standard deviations (FIG. 8). When the frequency distribution of the effects of A and F was studied in males and females respectively, we found a bimodal distribution. The significance of this observation is being studied at this point.

E, a stereoisomer of F, does not stimulate the VNO in female subjects while F does (FIG. 8B). This is a demonstration of the specificity of VNO recognition of vomeropherins. In this regard it is interesting to note that while F is a superior vomeropherin, E generates a stronger olfactory effect than does F (FIG. 8B and FIG. 9).

Effects of Vomeropherins on the EOG

Figure 9A:
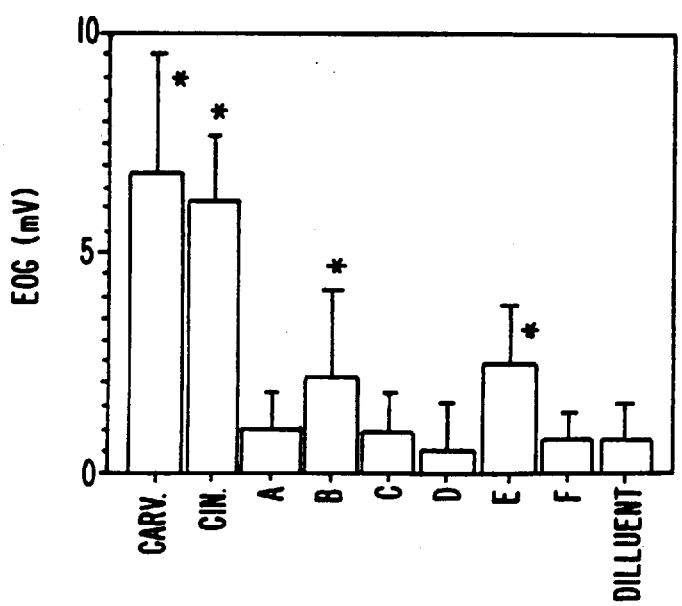
FIG. 9 depicts electro-olfactgrams of male and female subjects induced by stimulation of the OE with olfactants and vomeropherins A:400 fmoles of the olfactants 1-carvone and cineole as well as 200 fmoles of the vomeropherins A, B, C, D and F; and the stereoisomer E were applied separately as one second pulses to the OE of 20 subjects (both male and female) and each EOG response was recorded as described. The olfactants as well as E and B produced significant (p<0.01) local response. B:400 fmoles of the olfactants 1-carvone and cineole do not induce a significant EVG response when delivered to the VNO of male and female subjects.

The summated receptor potential from the olfactory epithelium (OE) was recorded in 20 subjects:10 males and 10 females. In contrast to the sensitivity of the VNO to vomeropherins, the OE is less sensitive to these substances. This is true for both males and females (FIG. 9A). The mean receptor potential amplitude ranged from 2.3 mV to 0.78 ,mV. In this study, B was the only vomeropherin having significant effect in the OE (p<0.02). Of the subjects questioned about odorant sensations following each stimulus presentation, 16 reported no olfactory sensation, while three males and one female described B as an unpleasant odor. This finding reveals that at the concentrations used in our study, most vomeropherins are not effective stimulants of the olfactory receptors, but do have a clear effect on vomeronasal receptors.

Effects of Olfactants on the EVG and EOG

Figure 9B:
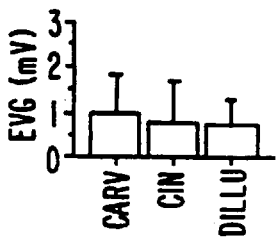

In contrast to vomeropherins, the olfactants 1-carvone and cineole produce only a minor local response in the VNO (FIG. 9B). This was true for both men and women. As expected, these olfactants produced a strong response in both men and women (p<0.01) when locally applied to the OE (FIG. 9A). The diluent depolarized olfactory receptors to a lesser extent than cineole or 1-carvone (p<0.01), and it did not produce an olfactory sensation.

Reflex Effects of Vomeropherins

Studies were conducted to determine the central nervous system (CNS) reflex responses to vomeropherin stimulation of the VNO. The sexually dimorphic local responses induced by vomeropherins (FIG. 8A and B) were mirrored in the autonomic response of male & female subjects. In male subjects (FIG. 8C), A and C decreased skin resistance (electrodermal activity=EDA) (p<0.01, n=30). In female subjects. (FIG. 8B), F and B produced greater decrease in EDA than A or C (p<0.01, n=30).

Vomeropherins A and C induced a significant increase in skin temperature (ST) (FIG. 8G) in 30 male subjects (p<0.01); however D induced significant temperature decrease (p<0.01). In 30 female subjects (FIG. 8H) B and F evoked a significant increase in skin temperature (ST) (p<0.01) compared to A and C. In female subjects vomeropherins produced changes in EDA and ST with a greater standard deviation than in males.

Figure 8G:
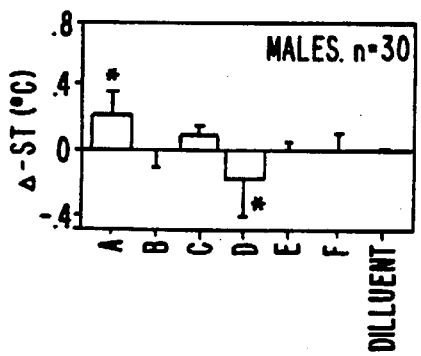
Figure 8H:
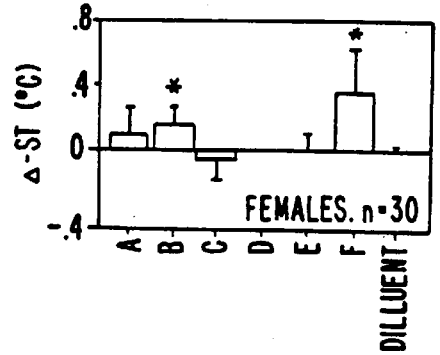
Figure 10A:
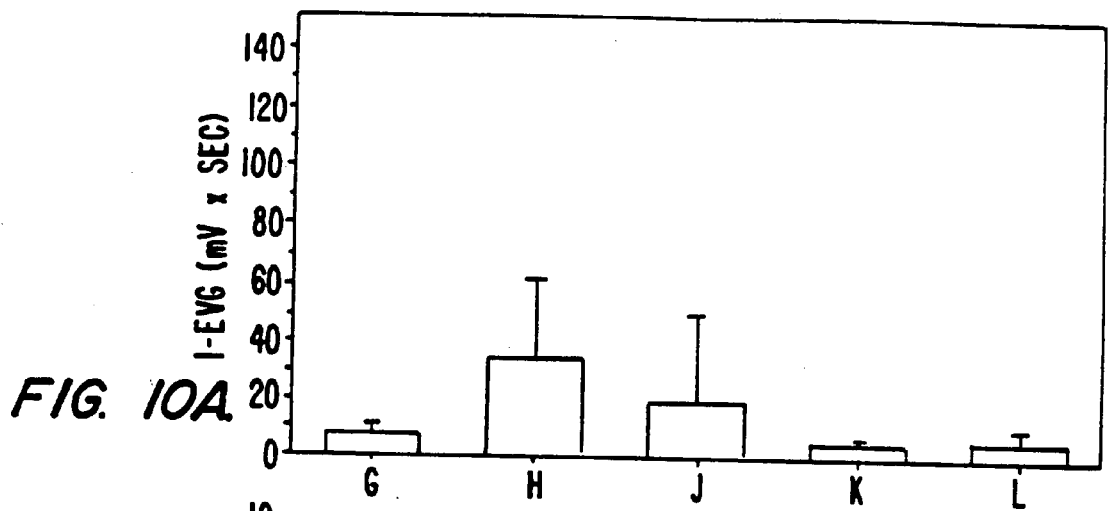
FIG. 10 depicts the electrophysiological effect of the following vomeropherins on the vomeronasal organ of 20 female subjects.
Figure 10B:
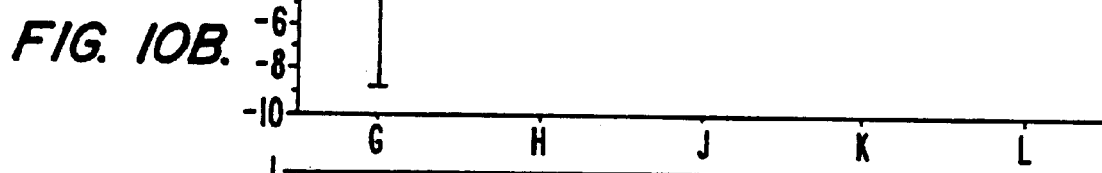
Figure 10C:
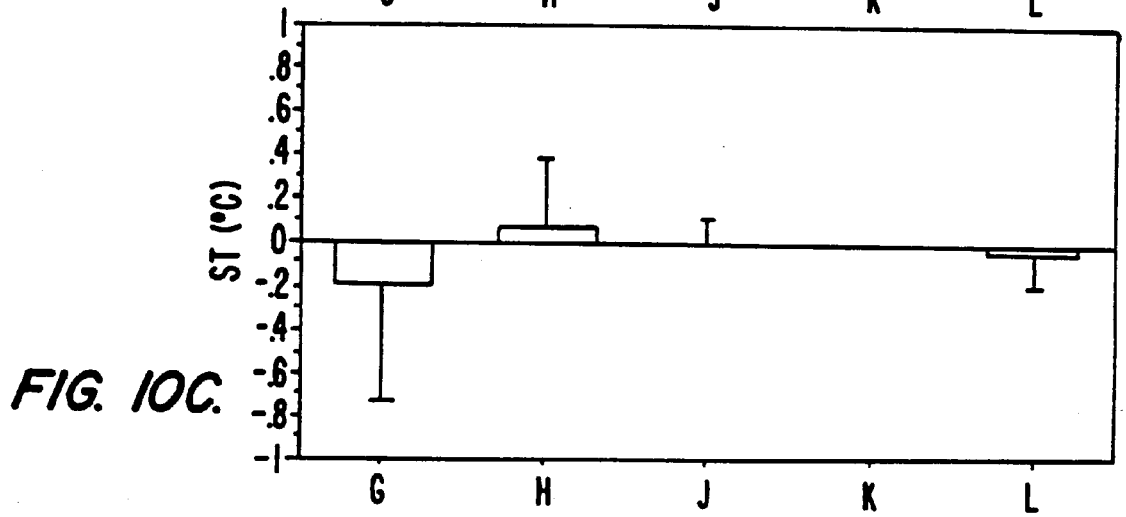
Figure 11A:
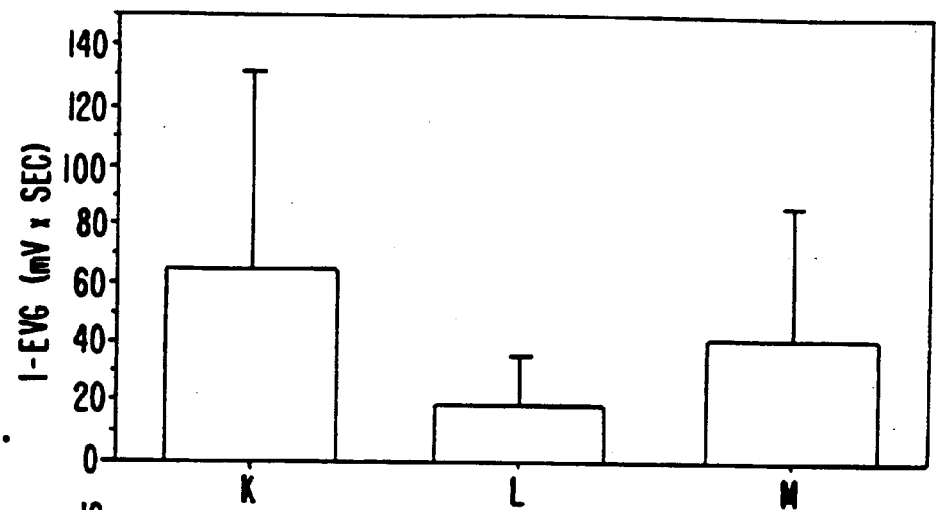
FIG. 11 depicts the electrophysiological effect of vomeropherins on the vomeronasal organ of 20 male subjects.
Figure 11B:
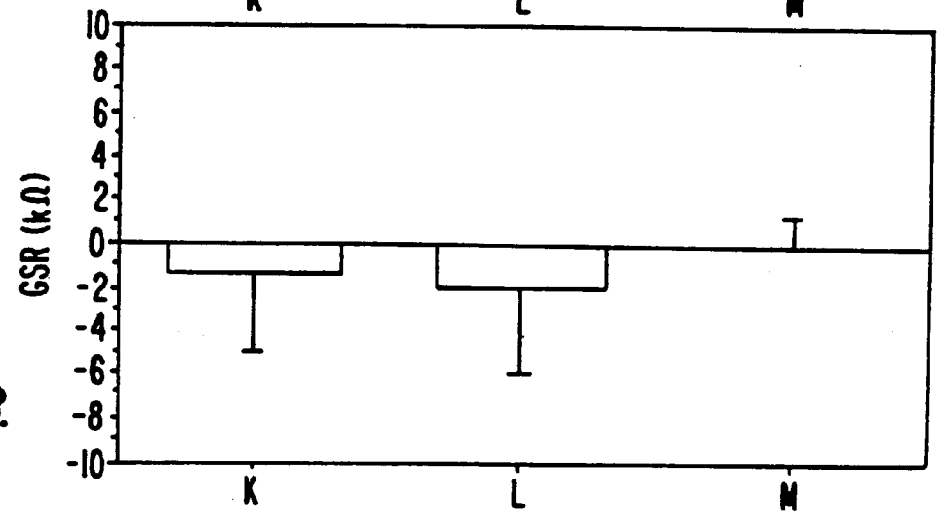
Figure 11C:
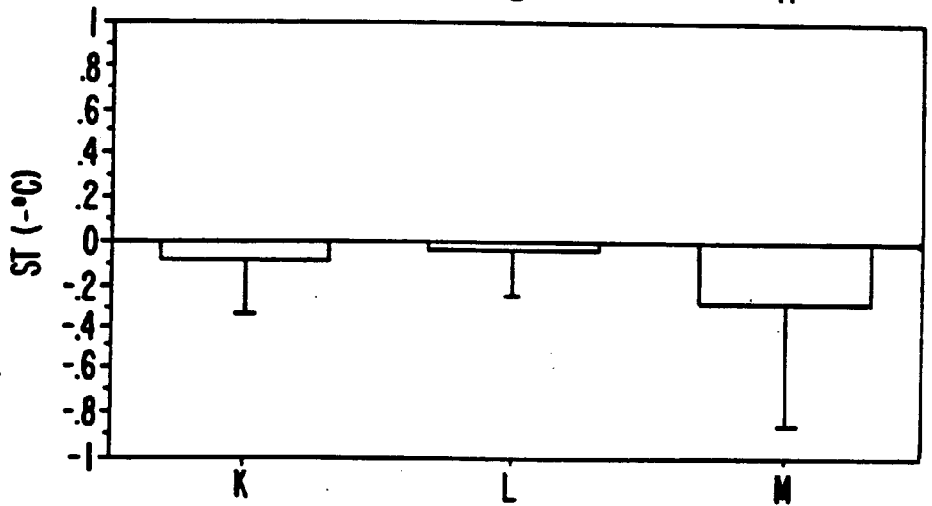

Cortical activity was recorded from Cz and Tz in male and female subjects during application to the VNO of air pulses (300 ms to 1 sec) containing 200 fmoles of vomeropherin (FIG. 8G and H). In males (FIG. 8E) A, C and D significantly increased alpha cortical activity with a latency of 270–380 ms. D and A evoked the strongest effect (p<0.01). Synchronization of the EEG was sustained for 1.5 to 2.7 minutes after application of a single pulse of active substance. In females (FIG. 8F), a single pulse (200 fmoles) of B or F applied to the VNO increased alpha cortical independent of the response of olfactory receptors. We found characteristic specificities in the response of the human VNO and the olfactory epithelium which suggests that they are independent functional systems with separate connections to the CNS (Brookover, C. (1914) The nervus terminalis in adult man. J. Comp. Neurol. 24:131–135.) There is also preliminary evidence that the EVG is not associated with trigeminal nociceptor endings since application of a local anesthetic (2% lidocaine) to the respiratory epithelium of the nasal septum neither blocks nor diminishes the EVG (Monti-Bloch, L. and Grosser, B. 1. (1991) "Effect of putative pheromones on the electrical activity of the human vomeronasal organ and olfactory epithelium," *J. Steroid Biochem. Molec. Biol.* 39:573–582.), also, subjects failed to report sensations of pain as a consequence of any of the stimulation procedures.

VNO receptors are clearly more sensitive to vomeropherins than to any of the olfactants tested; the opposite is true for olfactory receptors. While the OE may have receptor sites for some vomeropherins, the response specificity of the VNO is clearly different.

Sexual differences were noted in the specificities and effects of two groups of vomeropherins, A, C and D; and B and F. This suggests a possible receptor-related sexual dimorphism. The findings suggest the activation of components of the autonomic nervous system in the adult human by vomeropherin stimulation of the VNO.

Furthermore, the results suggest that stimulation of the VNO with vomeropherins produces synchronization of the EEG (FIG. 8G and H) Thus, the evidence herein indicates that the vomeronasal system responds to a variety of chemosensory stimuli, and that some are able to induce reflex autonomic activity.

We claim:

1. A method of reducing anxiety in an individual comprising the step of administering androsta-4,16-dien-3β-ol.

2. A method according to claim 1 wherein the androsta-4,16-dien-3β-ol is administered to the vomeronasal organ of said individual.

3. A method according to claim 1 wherein said individual is a woman.

4. A method of reducing anxiety in an individual comprising the step of administering to the vomeronasal organ of said individual a unit dosage of up to about 100 micrograms of androsta-4,16-dien-3β-ol.

5. A method according to claim 4 wherein the amount of androsta-4,16-dien-3β-ol that is administered is at least about 100 picograms but no more than about 100 micrograms.

6. A method according to claim 4 wherein the amount of androsta-4,16-dien-3β-ol that is administered is at least about 1 nanogram but no more than about 10 micrograms.

7. A method according to claim 4 wherein the amount of androsta-4,16-dien-3β-ol that is administered is at least about 10 nanograms but no more than about 1 microgram.

8. A method according to claim 4 further comprising preparing a pharmaceutical composition of the androsta-4,16-dien-3β-ol dissolved in a pharmaceutically acceptable carrier.

9. A method according to claim 8 wherein said pharmaceutical composition is an ointment.

10. A method according to claim 8 wherein said pharmaceutical composition is a liquid.

11. A method according to claim 4 wherein the administration is by aerosol.

12. A method according to claim 4 wherein said individual is a woman.

* * * * *